United States Patent
Dimond et al.

(10) Patent No.: US 6,369,207 B1
(45) Date of Patent: Apr. 9, 2002

(54) NUCLEIC ACID AMPLIFICATION WITH DNA-DEPENDENT RNA POLYMERASE ACTIVITY OF RNA REPLICASES

(75) Inventors: Randall L. Dimond, Madison; Steven J. Ekenberg, Mt. Horeb; James R. Hartnett, Madison; Geoffrey R. Hudson, Madison; Leopoldo G. Mendoza, Madison; Katharine M. Miller, Verona, all of WI (US); John E. Monahan, Walpole, MA (US); Christopher L. Jones; Mark A. Maffitt, both of Madison, WI (US); Richard A. Martinelli, Brighton, MA (US); Edward E. Pahuski, Marshall; James W. Schumm, Madison, both of WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/396,001

(22) Filed: Sep. 14, 1999

Related U.S. Application Data

(63) Continuation of application No. 08/480,041, filed on Jun. 6, 1995, now Pat. No. 6,090,589, which is a continuation-in-part of application No. 07/638,508, filed on Dec. 31, 1990, now abandoned.

(51) Int. Cl.[7] .................. C07H 19/00; C07H 21/00; C07H 21/02
(52) U.S. Cl. .................. 536/22.1; 536/23.1; 536/24.3; 536/24.33
(58) Field of Search ............ 536/22.1, 23.1, 536/24.3, 24.33

(56) References Cited

U.S. PATENT DOCUMENTS

| | | | |
|---|---|---|---|
| 4,786,600 A | 11/1988 | Kramer et al. ............... | 435/235 |
| 4,957,858 A | 9/1990 | Chu et al. ..................... | 435/6 |
| 5,112,734 A | 5/1992 | Kramer et al. ................. | 435/6 |
| 5,480,784 A | 1/1996 | Kacian et al. ........... | 435/91.21 |

FOREIGN PATENT DOCUMENTS

| | | |
|---|---|---|
| EP | 0 200 362 | 12/1986 |
| WO | WO 88/10315 | 12/1988 |
| WO | WO 89/10413 | 11/1989 |
| WO | WO 90/02819 | 3/1990 |
| WO | WO 90/02820 | 3/1990 |
| WO | WO 90/06995 | 6/1990 |
| WO | WO 90/14439 | 11/1990 |

OTHER PUBLICATIONS

Schaffner et al. "Nanovariant RNAs: Nucleotide Sequence and Interaction with Bacteriophage Q Replicase." J. Mol. Biology, 1977, 117, pp. 877–907.*

Gulati, S.C., et al., "Conditions for using DNA Polymerase I as an RNA–Dependent DNA Polymerase," Proc. Nat. Acad. Sci., vol 71, No. 4, pp. 1035–1039 (1974).

Feix, G. and Hake, H. "Primer Directed Initiation Of RNA Synthesis Catalysed by Qβ Replicase" Biochem. and Biophys. Res. Comm. (1975) 65:503–509.

Feix, G. and Sano, H. "Polydeoxyribonucleotides Templates for RNA Synthesis Catalysed by Qβ Replicase" FEBS Letters (1976) 63(1):201–204.

Feix, G. H. "Primer–Dependent Copying of Rabbit Globin mRNA with Qβ Replicase" Nature, (1976) 259:593–594.

Vournakis, J.N., Carmichael, G.C., and Efstratiadis, A. "Synthesis of RNA Complementary to Rabbit Globin mRNA by Qβ Replicase," Biochem. and Biophys. Res. Comm. (1976) 70:774–782.

Blumenthal, T. and Carmichael, G.G. "RNA Replication: Function and Structure of Qβ–Replicase," Ann. Rev. Biochem. (1979) 48:525–548.

Miele, et al., "Autocatalytic Replication of a Recombinant RNA," Journal of Molecular Biology, vol. 171, pp. 281–295 (1983).

Chu, et al., "Synthesis of an amplifiable reporter RNA for bioassays," Nucleic Acids Research, vol. 14, No. 14, pp. 5591–5603 (1986).

Sharmeen, Lamia and Taylor, John, "Enzymatic synthesis of RNA oligonucleotides," Nucleic Acids Research, vol. 15, No. 16, pp. 6705–6711 (1987).

Milligan, John F., et al., "Oligoribonucleotide using T7 RNA polymerase and synthetic DNA templates," Nucleic Acids Research, vol. 15, No. 21, pp. 8783–8799 (1987).

Tabor, Stanley and Richardson, Charles C., "Effect of manganese ions on the incorporation of dideoxynucleotides by bacteriophage T7 DNA polymerase and *Escherichia coli* DNA polymerase I," Proc. Natl. Acad. Sci., vol. 86, pp. 4076–4080 (1989).

* cited by examiner

*Primary Examiner*—Jezia Riley
(74) *Attorney, Agent, or Firm*—Foley & Lardner

(57) ABSTRACT

The present invention entails methods, and kits for carrying them out, based on the discovery that an RNA replicase, such as Qβ replicase, has DNA-dependent RNA polymerase ("DDRP") activity with nucleic acid segments, including DNA segments and DNA:RNA chimeric segments, which comprise a 2'-deoxyribonucleotide or an analog thereof and which have sequences of RNAs that are autocatalytically replicatable by the replicase. The discovery of this DDRP activity provides methods of the invention for nucleic acid amplification wherein a nucleic acid, with a DNA segment with the sequence of an RNA that is autocatalytically replicatable by an RNA replicase, is provided as a substrate for the replicase. The replicase catalyzes synthesis, from the DNA segment, of the RNA, which the replicase then autocatalytically replicates. The invention entails use of the amplification methods in detecting nucleic acid analytes, as in nucleic acid probe hybridization assays. Such assays of the invention include those wherein a nucleic acid analyte is hybridized with one or more nucleic acid probes, which include or are processed to generate a DNA segment which is amplifiable through production from the segment, catalyzed by the DDRP activity of an RNA replicase, of an autocatalytically replicatable RNA, which is autocatalytically replicated to provide an abundance of readily detectable reporter molecules. The invention permits replacement of an RNA, that is autocatalytically replicatable with an RNA replicase and employed as a reporter or label in prior art assays, such as nucleic acid probe hybridization assays or immunoassays, with a nucleic acid comprising a DNA segment with the same base sequence as the RNA. The invention also includes the methods of the invention with $Mn^{+2}$, $Co^{+2}$, or $Zn^{+2}$ in the solutions in which the DDRP activity occurs.

11 Claims, 10 Drawing Sheets

(a)

(b)

(c)

(d)

———— = REPLICASE AMPLIFIABLE SEGMENT
∿∿∿∿ = ANTI-TARGET SEGMENT
════ = CONNECTING SEGMENT
▬ = REPORTER SEGMENT

```
           SphI         T7 Promoter
5'-AAGCTTGCAT GCCTGCAGTA ATACGACTCA CTATAGGGGA AATCCTGTTA
   HindIII      PstI CCAGGATAAC GGGGTTTTCT CACCTCTCTA CTCGAAAGTT AGAGAGGACA
                   nanovariant (+) strand SmaI         SstI
   CACCCGGATC TAGCCGGGTC AACCCGGGTA CCGAGCTCGA ATTC-3'
                                KpnI          EcoRI
```

PLASMID CONTAINING mdv-XhoI SEQUENCE

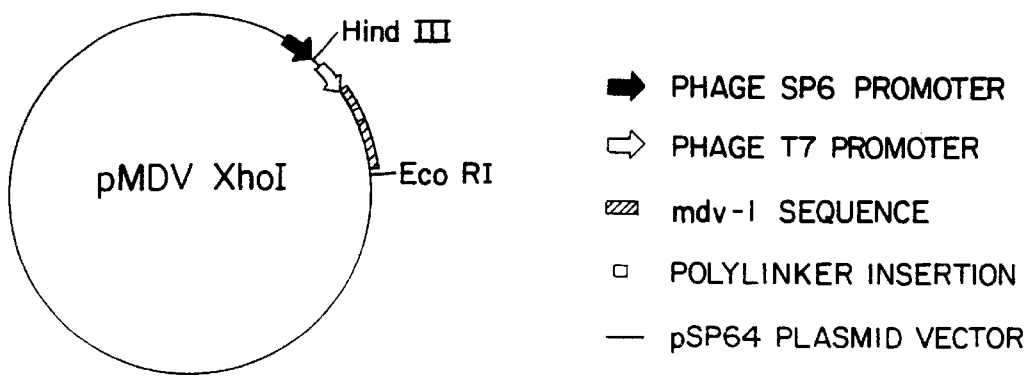

➡ PHAGE SP6 PROMOTER
⇨ PHAGE T7 PROMOTER
▧ mdv-I SEQUENCE
▫ POLYLINKER INSERTION
— pSP64 PLASMID VECTOR HindIII to EcoRI DNA Sequence

```
HindIII     PstI         T7 Promoter
AAGCTT   gGG CTGCAG TC TAATACGACTCACTATA GGGGACCCCCCCGGAAgGGG
                                         ........10........20

GGGACGAGGTGCGGGCACCTGCTACGGGAGTTCGACCGTGACGAG CCTCGAGGAG TCACG
........30........40........50........60..... ...70..... ...80

GGCTAGCGCTTTCGCGCTCTCCCAGGTGACGCCTCGTGAAGAGGCGCGACCTTCGTGCGT
........90........100.......110.......120.......130.......140

TTCGGTGACGCACGAGAACCGCCACGCTGCTTCGCAGCGTGGCcCCTTCGCGCAGCCCGC
........150.......160.......170.......180.......190.......200
                                              SmaI    EcoRI
TGCGCGAGGTGACCCCCCGAAGGGGggtTCCC GGGAATTC
........210.......220.......230.. .....240
```

Midivariant and insertion sequences are enumerated.
Insertion sequences are underlined.
Ambiguities in the sequence data are shown in lower case letters.

NUCLEIC ACID AMPLIFICATION WITH DNA-DEPENDENT RNA POLYMERASE ACTIVITY OF RNA REPLICASES

This application is a continuation of U.S. application Ser. No. 08/480,041 filed on Jun. 6, 1995, which issued as U.S. Pat. No. 6,090,589, and which is a continuation-in-part of U.S. application Ser. No. 07/638,508 filed on Dec. 31,1990, entitled NUCLEIC ACID AMPLIFICATION WITH DNA-DEPENDENT RNA POLYMERASE ACTIVITY OF RNA REPLICASES, now abondoned.

FIELD OF THE INVENTION

The present invention is directed to a method and a kit for amplifying nucleic acid segments and detecting nucleic acid analyte in a test sample. More specifically, the present invention relates to amplifying nucleic acid segments using the DNA-dependent RNA polymerase activity of RNA-dependent RNA replicases, such as Qβ replicase, and detecting the products of such amplification.

BACKGROUND OF THE INVENTION

The ability to detect specific target nucleic acid analytes using nucleic acid probe hybridization methods has many applications. Among these applications are diagnoses of infectious or genetic diseases or cancer in humans or other animals; identification of viral or microbial contamination of cosmetics, food or water; and identification or characterization of, or discrimination among, individuals at the genetic level, for forensic or paternity testing in humans and breeding analysis and stock improvement in plants and animals. The basis for applications of nucleic acid probe hybridization methods is the ability of an oligonucleotide or nucleic-acid-fragment probe to hybridize, i.e., form a stable, double-stranded hybrid through complementary base-pairing, specifically with nucleic acid segments which have a particular sequence and occur only in particular species, strains, individual organisms or cells taken from an organism.

One of the basic limitations in nucleic acid probe hybridization assays has been the sensitivity of the assays, which depends on the ability of a probe to bind to a target molecule and on the magnitude of signal that is generated from each probe that binds to a target molecule and that can be detected in a time period available for detection. Known detection methods in the assays include methods dependent on signal generated from a probe, as from fluorescent moieties or radioactive isotopes included in the probe, or an enzyme, such as an alkaline phosphatase or a peroxidase, linked to the probe and, after probe hybridization and separation of hybridized from unhybridized probe, incubated with a specific substrate to produce a characteristic colored product. However, the practical detection limit of these assays is about 200,000 target molecules (3 femtomolar concentration in 100 μl), which is not sufficiently sensitive for many applications. Much effort is therefore being expended in increasing the sensitivity of detection systems for nucleic acid probe hybridization assays.

A second area of research which is receiving significant attention is enhancement of sensitivity by, in effect, increasing the number of target molecules to be detected, i.e., by the amplification of a segment of target nucleic acid to quantities sufficient to be readily detectable using currently available signal-producing and signal-detection methods. The traditional method of obtaining increased quantities of target molecules in a sample has been to grow an organism with the target molecule under conditions which enrich for the organism using various culturing methods. (Lennette, E. H., et al. (1985), Manual of Clinic Microbiology, editors, American Society for Microbiology, Washington, D.C.; Gerhardt, P., et al. (1981), Manual of Methods for General Bacteriology, Editors, American Society for Microbiology, Washington, D.C.). Recent advances in increasing the number of target molecules in a sample have focused on target-dependent increases in the number of reporter molecules which can be derived from individual target molecules. Such a "reporter molecule" may or may not have the sequence of a segment of the corresponding target molecule. One example of these recent advances is amplification using the so-called "polymerase chain reaction" ("PCR"). With respect to PCR amplification, reference is made to Current Protocols in Molecular Biology, Suppl. 4, Section 5, Unit 3.17, which is incorporated herein by reference, for a basic description of PCR. Other references which describe PCR include Erlich, H. A., (Ed.) 1989, PCR Technology, Stockton Press; Erlich, H. A., et al. (1988), Nature 331:461–462; Mullis, K. B. and Faloona, F. A. (1987), Methods in Enzymology, 155:335–350; Saiki, R. K., et al. (1986), Nature 324:163–166; Saiki, R. K., et al. (1988), Science 239:487–491; Saiki, R. K., et al. (1985), Science 230:1350–1354; U.S. Pat. No. 4,683,195 to Mullis, et al.; and U.S. Pat. No. 4,683,202 to Mullis.

In PCR, the double-stranded target nucleic acid is thermally denatured and hybridized with a pair of primers which flank the double-stranded segment of interest in the target (one primer hybridizing to the 3'-end of each strand of this double-stranded segment) and then the primers are extended in a DNA polymerase-catalyzed extension reaction. Numerous (e.g., typically twenty-five) cycles of the denaturation, hybridization and primer-extension process generate, for each target molecule in a sample of nucleic acids, many copies of reporter molecules, which are double-stranded DNAs with the same nucleic acid sequence as a segment (usually of about 100–2000 base pairs) of the target molecule. In a twenty-five cycle PcR amplification, more than about $10^6$ reporter segments can be generated for each target molecule present initially in a sample. The PCR process is cumbersome because of the need to perform many cycles of the reaction, which usually require two or more hours for sufficient amplification. Additionally, the amplification process is more time-consuming if it is carried out manually. Further, it can be quite expensive if automated equipment is used.

Another recently disclosed amplification process, called the "transcription-based amplification system" ("TAS"), uses primers which comprise segments for a promoter, which is recognized specifically by a DNA-dependent RNA polymerase which can produce quickly a large number of transcripts from segments operably linked for transcription to the promoter. Reference is made to Gingeras, T. R., et al., PCT Patent Publication No. WO 88/10315. Using suitable primers and primer-extension reactions with a single-stranded target molecule (e.g., an RNA or one strand of a double-stranded DNA) generates a double-stranded product which has a promoter operably linked for transcription to a pre-selected segment of the target molecule. Transcription of this product with a DNA-dependent RNA polymerase that recognizes the promoter produces, in a single step, 10 to 1,000 copies of an RNA comprising a sequence complementary to that of the target segment (i.e., the preselected segment of target molecule). Two additional rounds of primer extension using a reverse transcriptase enzyme and the RNA copies made in the initial transcription step produce CDNA copies which are ready for additional amplification by transcription using the DNA-dependent RNA polymerase to yield RNA with the same sequence as the target segment of target molecule. Additional cycles of cDNA synthesis and transcription can be performed. While TAS amplification, like PCR, makes a large number of reporter molecules (RNA in the case of TAS), which have the same sequence as a segment of the target molecule or the sequence complementary thereto, and uses fewer steps than PCR to achieve the same level of amplification, TAS requires two more enzymatic reactions, i.e., DNA-dependent RNA polymerase-catalyzed transcription and reverse transcription, and one or two more enzymes (DNA-dependent RNA polymerase and, if not used for primer-dependent DNA extension, reverse transcriptase) than PCR. Additionally, no time savings in comparison with PCR is claimed.

A third amplification procedure, which entails a form of amplification of label attached to a probe rather than amplification of a segment or segments of target nucleic acid analyte, is based on the use of the Qβ replicase enzyme and its RNA-dependent RNA polymerase activity. Reference is made to Blumenthal, T. and G. G. Carmichael (1979), Ann. Rev. Biochem. 48:525–548; PCT Patent Publication No. WO 87/06270 and U.S. Pat. No. 4,957,858 to Chu, B., et al.; Feix, G. and H. Sano (1976), FEBS Letters 63:201–204; Kramer, F. R. and P. M. Lizardi (1989), Nature 339:401–402; U.S. Pat. No. 4,786,600 to Kramer; Lizardi, P. M., et al. (1988), Biotechnology 6:1197–1202; and Schaffner, W., et al. (1977), J. Mol. Biol. 117:877–907 for a further description of this procedure. In the procedure, a replicative (sometimes referred to as "replicatable") RNA molecule is covalently joined to a specific hybridizing probe (i.e., a single-stranded nucleic acid with the sequence complementary of that of a segment ("target segment") of target nucleic acid analyte in a sample). The probe may be a segment embedded within a recombinant replicative RNA or attached to one of the ends of a replicative RNA. The probe-replicatable RNA complex hybridizes (by means of the probe segment) to target nucleic acid analyte in a sample, and the probe-RNA complexes that have hybridized are then separated from those that have not, and the replicatable RNAs of the complexes that did hybridize to target are then (typically after separation from probe segment if probe segment was not embedded in the replicatable RNA) amplified exponentially by incubation with Qβ replicase, which catalyzes autocatalytic replication of the replicatable RNA to produce up to $10^9$ reporter molecules (replicatable RNAs) for each hybridized target molecule. Such amplification can be completed in 30 minutes (Lizardi, et al., supra).

The extreme specificity of Qβ replicase for RNAs with certain structural and sequence requirements for catalysis of autocatalytic replication assures that only the replicatable RNA associated with probes is amplified (Kramer and Lizardi, supra, 1989). Other advantages include the speed of the reaction and the simplicity of manipulations. However, a disadvantage includes the need to use RNA as a reporter molecule. An RNA of a given sequence is more expensive to manufacture and more sensitive to heat-stable nucleases than the DNA with the same sequence. In addition, except in cases where a probe segment can be embedded in a replicative RNA, the target segment is not amplified with the reporter molecules.

SUMMARY OF THE INVENTION

The present invention rests on the discovery of a DNA-dependent RNA polymerase ("DDRP") activity of Qβ replicase, the enzyme which catalyzes replication of the genome of the bacteriophage Qβ, and functional equivalents thereof (e.g., other RNA-dependent RNA replicases that have DDRP activity). The discovery of this DDRP acytivity allows the use of substrates which comprise 2'-deoxyribonucleotides or analogs thereof, including DNA substrates, for amplification by Qβ replicase and the other replicases with DDRP activity.

The DDRP activity of an RNA replicase results in production of an RNA (or a polyribonucleotide in which, at some positions, ribonucleotide analogs are present), that is autocatalytically replicatable by the RNA replicase, from any substrate, which comprises a segment with the sequence of the autocatalytically replicatable RNA and which includes, within the segment with this autocatalytically replicatable sequence, a 2'-deoxyribonucleotide or an analog thereof, such as a 2'-deoxyriboalkylphosphonate, 2'-deoxyribophosphorothioate, 2'-deoxyribophosphotriester, or 2'-deoxyribophosphoramidate. In a substrate for the DDRP activity of an RNA replicase, the segment, which acts as the template for synthesis, catalyzed by the replicase, of the auto-catalytically replicatable RNA, can be a segment which encompasses the entire substrate (and, therefore, includes both the 3'-end and the 5'-end of the substrate), a segment which includes the 3'-end but not the 5'-end of the substrate, a segment which includes the 5'-end but not the 3'-end of the substrate, or a segment embedded within the substrate (and, therefore, including neither the 3'-end nor the 5'-end of the substrate). The substrate can be linear or closed circular and may be part of a double-stranded nucleic acid. The segment or the substrate may consist entirely of 2'-deoxyribonucleotides (i.e., a DNA segment or substrate, respectively). The substrates with which the DDRP activity is operative are not limited to homopoly-2'-deoxyribonucleotides, such as poly-dAs, with poly-dC segments at their 3'-ends, or RNAs with poly-dC segments at their 3'-ends. See Feix and Sano (1976), supra.

In the methods of the present invention, the substrates for the DDRP activity of RNA replicases are "complex" substrates. A "complex" substrate is one which is a closed circle, which does not have a free 3'-end; or one which has a free 3'-end but wherein the segment, which is the template for synthesis of an autocatalytically replicatable RNA catalyzed by the DDRP activity, does not include the 3'-end; or one which has a free 3'-end and wherein the segment, which is the template for synthesis of an autocatalytically replicatable RNA catalyzed by the DDRP activity, includes the 3'-end but has a segment other than a poly-dC at the 3'-end; or one which has a free 3'-end and wherein the segment, which is the template for synthesis of an autocatalytically replicatable RNA catalyzed by the DDRP activity, includes the 3'-end and has a poly-dC at its 3'-end but has, as the subsegment of said segment, other than the poly-dC at the 3'-end, a subsegment which comprises at least one 2'-deoxyribonucleotide or analog thereof but is not an homopoly-2'-deoxyribonucleotide. The segment, which is the template in a complex substrate for synthesis of an autocatalytically replicatable RNA catalyzed by the DDRP activity of an RNA replicase, is referred to as a "complex segment" or "complex template." In the methods of the invention, the "complex segments" comprise at least one 2'-deoxyribonucleotide or analog thereof.

Reference herein to a "poly dC" means a segment of at least two dC's.

Reference herein to a "2'-deoxyribonucleotide" means one of the four standard 2'-deoxyribonucleotides.

Reference herein to a "2'-deoxyribonucleotide analog" means an analog of a 2'-deoxyribonucleotide, which analog (i) has, as the base, the base of the 2'-deoxyribonucleotide or said base derivatized at a ring carbon or an amino nitrogen; and (ii) is other than the corresponding, standard ribonucleotide (rA for dA, rC for dC, rG for dG, U for T). A 2'-deoxyribonucleotide analog, that is part of a template for DDRP activity by an RNA replicase in accordance with the invention, will be recognized by the replicase in the template to place the ribonucleotide with the base, that is complementary to that of the 2'-deoxyribonucleotide, in the corresponding position of the autocatalytically replicatable RNA made from the template via the DDRP activity.

The RNA (or polyribonucleotide with one or more ribonucleotide analogs) made as a result of the DDRP activity of an RNA replicase is autocatalytically replicatable by the replicase (or another RNA-dependent RNA replicase which recognizes the RNA copies as templates for autocatalytic replication). Thus, a segment that is a template for the DDRP activity of an RNA replicase, is amplified, in the presence of the replicase, the ribonucleoside 5'-triphosphates, and, possibly, analogs of certain of the ribonucleoside 5'-triphosphates, because RNA (or polyribonucleotide with one or more ribonucleotide analogs) that is made in the synthesis catalyzed by the DDRP activity is autocatalytically replicated by the same replicase.

In its most general sense, then, the invention is a method for amplifying complex nucleic acid templates using the DNA-dependent RNA polymerase activity of RNA replicases, such as that of bacteriophage Qβ. The invention also entails numerous applications of this amplification method in making, amplifying, detecting, sequencing or otherwise treating a nucleic acid of interest. Thus, the amplification process can be used to make large amounts of RNA, which, for example, can be used as a nucleic acid probe, converted to CDNA for cloning, detected as part of a nucleic acid probe hybridization assay, or sequenced.

The amplification method of the invention can be employed with a sample of nucleic acid in a target-dependent manner, such that an autocatalytically replicatable RNA which has, or comprises a segment with, a pre-determined sequence will be produced at a level detectable above background in the amplification carried out with the sample only if a "target" segment of nucleic acid (i.e., a segment with a pre-determined "target" sequence) is present in the sample. Thus, the invention entails a method for target nucleic acid segment-directed amplification of a reporter nucleic acid molecule which comprises using the DDRP activity of Qβ replicase, or another replicase having DDRP activity. More specifically, to a sample of nucleic acid, one or more nucleic acid probes are added and the sample with the probes is processed such that a complex substrate for the DDRP activity of an RNA replicase, such as Qβ replicase, occurs if and only if a target nucleic acid comprising one or more target segments occurs in the sample. This complex substrate is, or comprises, a complex segment which, in turn, comprises a pre-determined sequence (which is or comprises a reporter sequence) and which is the template for the DDRP activity. Each of the probes will hybridize to a target segment or the complement of a target segment and the probes will comprise segments such that, upon suitable processing, a nucleic acid that is the complex substrate for DDRP activity can be made using the probes if and only if the target segment(s) is (are) present in the sample. Once the sample has been treated so that substrate for DDRP activity occurs, if target nucleic acid is present, an RNA replicase, which has such activity with the substrate, is added, along with other reagents necessary for reactions catalyzed by the replicase, to an aliquot of the sample. If target nucleic acid was present, so that substrate for the DDRP activity was produced, autocatalytically replicatable RNA, which will have or comprise the reporter sequence or the sequence complementary thereto, will be amplified to detectable levels by the DDRP activity coupled with the autocatalytic replication of the RNA made with the DDRP activity. If target nucleic acid was not present, no substrate for the DDRP activity will be produced which comprises the reporter sequence and the replicase will not yield autocatalytically replicated RNA with such reporter sequence (or the sequence complementary thereto). RNA with such reporter sequence serves as a "reporter" directly or, if further processed, indirectly. Thus, production of the RNA constitutes amplification of a reporter molecule and the process is target-directed (i.e., target-dependent).

The present invention provides methods for detecting the presence or absence of a target nucleic acid analyte in a sample containing nucleic acid. These methods of the invention comprise target-directed amplification in accordance with the invention, with the DDRP activity of Qβ replicase, or other replicase with DDRP activity, of reporter nucleic acid, and assay for reporter nucleic acid.

Among advantages provided by certain of the methods according to the invention for detecting nucleic acid analyte is a reduction in the frequency of "false positives" that occur in assays that employ such methods of the invention in comparison with assays that employ other methods. This advantage is associated with the fact that DNA is amplifiable (more precisely, capable of initiating amplification) using the DDRP activity of Qβ and other replicases in connection with assay systems, and DNAs can be modified in specific ways using enzymes which do not modify RNAs in the same ways, if at all.

Several different embodiments of the target-dependent amplification methods of the invention are provided. These embodiments depend on different structures of, and methods of treating, the various nucleic acid probes employed to provide in a sample of nucleic acid, in a manner dependent on the presence of target nucleic acid in the sample, a complex nucleic acid segment which is amplifiable using the DDRP activity of an RNA replicase.

In one embodiment, to a sample of nucleic acid, which may include nucleic acid comprising a pre-selected target segment, a nucleic acid probe is added which comprises both a replicase-amplifiable, complex segment, which, as indicated above, comprises at least one 2'-deoxyribonucleotide, and an anti-target ("probing") segment, which has the sequence complementary to that of the target segment. The nucleic acid probe that hybridizes to target segment, if any, in the sample is separated from probe that did not hybridize and hybridized probe is treated under amplification conditions in the presence of Qβ replicase, or another replicase exhibiting a DDRP activity with the replicase-amplifiable segment of the probe, resulting in the target-dependent production and amplification of reporter nucleic acid molecules. The process may also include the step of determining whether amplification has occurred.

In another embodiment, similar to that just described, the separation of probe hybridized to target from that not so hybridized is accomplished by subjecting the nucleic acid of the sample, after hybridization of probe to any target that may be present, to the action of a nuclease that will digest the replicase-amplifiable segment of any unhybridized probe. In this embodiment, in which probe, if hybridized, is protected from digestion, as in other embodiments of target-dependent amplification processes in accordance with the invention, if the amplification process is part of an assay for target analyte, amplified material will be tested for using any of the many methods known to the skilled.

In another embodiment, the target nucleic acid segment is hybridized with two probes in such a fashion that, after hybridization with the target nucleic acid, the 3'-end of the anti-target segment of one of the probes will be adjacent to the 5'-end of the anti-target segment of the other probe. Each probe comprises a portion of a nanovariant DNA, or other amplifiable DNA, covalently linked to anti-target segment. In one probe, the anti-target segment is at the 5'-end and, in the other, at the 3'-end. Once hybridized, the probes may be ligated via the anti-target segments. Preferably, T4 DNA ligase or another suitable ligase is used for the ligation. After the ligation, if it is carried out, or the hybridization, if ligation is not carried out, the adjacent probes are amplified via the DDRP activity of Qβ replicase or a functional equivalent thereof. If the ligation/amplification process is, for example, part of a nucleic acid probe hybridization assay method, then, once amplification has been carried out, the amplified material is detected by a suitable means known to those skilled in the art. The amplified RNA, which comprises the sequence of the joined anti-target segments or the complement of that sequence, is a recombinant autocatalytically replicatable RNA wherein a segment, corresponding to the joined anti-target segments, is inserted into another RNA which is autocatalytically replicatable. Only if target segment was present in the sample will amplified RNA, which comprises the sequence of the joined anti-target segments or the complement of that sequence, be produced in the amplification process.

Two DNA probes are also employed in another embodiment of the invention. A first probe, for use in accordance with the embodiment, has a 3'-end which is an anti-target segment complementary (or nearly complementary) in sequence to a first target segment of target nucleic acid and is suitable for priming DNA synthesis using target nucleic acid as template. A second probe, for use in the embodiment, has a 3'-end which is a segment (termed a "target-like" segment) with the same (or nearly the same) sequence as a second target segment of target nucleic acid and also is suitable for priming DNA synthesis using the complement of target nucleic acid as template. The 3'-terminal nucleotide of said second target segment is located 5'- from the 5'-terminal nucleotide of said first target segment. Thus, the second probe can prime DNA synthesis on the primer extension product of the first probe annealed to target nucleic acid. The 5'-ends of both of the probes are replicase amplifiable or parts of nucleic acid that is replicase amplifiable, e.g., 5'-end of a nanovariant (+) DNA at the 5'-end of the first probe and 5'-end of a corresponding nanovariant (−) DNA at the 5'-end of the second probe. In the amplification process, the first probe is annealed to target and extended and the resulting extension products are preferably strand-separated by thermal denaturation, or if target is RNA, may be strand-separated by treatment with an enzyme providing RNase H activity. To the strand of the extension product which comprises the first probe at the 5'-end, the second probe is annealed and extended. Subsequent to, or simultaneously with, extension of second probe, amplification is catalyzed with the DDRP activity of Qβ replicase or equivalent. If, but only if, target nucleic acid or its complement is present in a sample of nucleic acid with which this dual primer extension/amplification process is carried out, amplified product will include nucleic acid which comprises (i) the complement of the anti-target segment of the first probe, (ii) the target-like segment of the second probe, and (iii) the same segment, if any, between the segments of (i) and (ii) as occurs between the two target segments in target nucleic acid. Thus, a nucleic acid probe hybridization assay method of the invention is provided by following the dual primer extension/amplification process by any conventional assay for amplified product which comprises these two, or three, segments.

In another embodiment of the invention, a probe can be employed which is referred to for convenience as an "RNA probe" but which either consists entirely of ribonucleotides (and is an RNA probe) or comprises in its sequence a sufficient number of ribonucleotides to permit degradation with a ribonuclease or chemical treatment that degrades RNA but DNA, if at all, at a much slower rate. The RNA probe comprises an anti-target segment, which is complementary or nearly complementary in sequence to a target segment, which is at the 3'-end of target nucleic acid or a segment thereof, so that target segment can prime DNA synthesis on the RNA probe as template. At its 5'-end the RNA probe comprises a replicase amplifiable segment. The target nucleic acid is treated so that the 3'-end of the target segment is "free," i.e., its 3'-terminal nucleotide has a 3'-hydroxyl and is at the end of a nucleic acid and not covalently joined, except through its 5'-carbon, to another nucleotide. The free 3'-end of target segment is preferably provided by any conventional technique by treating target nucleic acid prior to annealing RNA probe to target (or part thereof). The probe, and any target in the system, are combined under hybridizing conditions, the target segment is extended in a primer-extension reaction catalyzed by the reverse transcriptase activity of an enzyme which has such activity, and the RNA in the system is then degraded chemically or using enzymes with RNase activities, as understood in the art. This degradation of RNA is sufficiently extensive, when coupled with dilution that might also be carried out, to diminish the concentration of RNA probe that retains a replicase-amplifiable segment and that thereby is operative, as a template for amplification by the replicase to be employed subsequently in the process, to a sufficiently low level that amplification of any such probe that might remain in an aliquot of sample on which amplification is carried out will not be observable. Typically, after the reverse transcription of the RNA probe, the solution (or an aliquot thereof) will be treated so that the concentration of amplifiable-segment-retainng RNA in the aliquot of carried out will be less than 1/1000, and preferably less than 1/10,000, the concentration of complex template for DDRP activity that will be present if target segment was present in the sample of nucleic acid to which the amplification process is applied. More preferably, degradation of RNA will be coupled with dilution so that, statistically, less than one molecule of RNA with an amplifiable segment remains in the aliquot on which amplification is carried out. Any DNA-extension product remaining after target segment extension and RNA degradation comprises a repicase-amplifiable, complex DNA segment. After degradation of RNA in the system, and substantial elimination of RNA-degrading conditions or activities, the DDRP activity of Qβ replicase or a functional equivalent is employed to amplify the replicase amplifiable segment added to any target DNA. Amplification will occur only if target segment, capable of priming DNA extension reaction on RNA probe as template, was present in a sample being tested. Thus, by applying after the amplification reaction any conventional method to test for the presence of amplified product, a method of assaying for target nucleic acid is also provided.

An RNA probe, which may consist entirely of ribonucleotides or comprises in its sequence a sufficient number of ribonucleotides to permit degradation with a ribonuclease or chemical treatment that degrades RNA but not DNA, can be employed in another embodiment of the invention, wherein three probes are employed. The first probe, which can be DNA or RNA or chimeric (i.e., any combination of ribonucleotides and 2'-deoxyribonucleotides or analogs of either), comprises at its 5'-end a first anti-target segment with the sequence complementary to or nearly complementary to that of a first target segment of target nucleic acid. The first probe must hybridize to its corresponding target segment with sufficient stability to block chain-extension of a second probe, as presently described. The second probe, which also can be DNA or RNA or chimeric, compromises a second anti-target segment at its 3'-end with the sequence complementary to, or nearly complementary to, that of a second target segment of target nucleic acid and, when annealed to target nucleic acid, is capable of priming DNA synthesis, using target nucleic acid as template. The 3'-end of the first target segment is located 5' from the 5'-end of the second target segment and is separated from the 5'-end of the second target segment by a gap of at least several, and up to about 2000, bases. The third probe is referred to for convenience as an RNA probe but, like the RNA probe described above, which comprises a replicase-amplifiable segment, must only comprise a sufficient number of ribonucleotides to be susceptible, through processes which degrade RNA, to having eliminated the replicase-amplifiability of its replicase-amplifiable segment. The third probe comprises a target-like segment at its 3'-end and a replicase amplifiable segment. The target-like segment has the same or nearly the same sequence as a third segment of target nucleic acid, which comprises at its 5'-end at least several nucleotides of the gap between the first and second target segments (and may overlap the second target segment) and which has as its 5'-terminal base the base that is adjacent to the 3'-terminal base of the first target segment. The third probe, through the target-like segment, must be capable of priming DNA synthesis using as template the chain-extension product of the second probe, made using target nucleic acid as template. To amplify a reporter segment in accordance with the invention, in a target nucleic acid-dependent manner, the nucleic acid of a sample is rendered single-stranded and first and second probes are added to the sample, which is subjected to conditions whereby the probes will anneal to target if present and second probe, once annealed, will be extended in a primer-directed, template-dependent DNA extension reaction catalyzed by an enzyme such as Klenow Fragment of *E.coli* DNA polymerase I. The extension added to second probe in this extension reaction will have the sequence complementary to that of the gap between the first and second target segments in target nucleic acid. After the extension reaction, the sample is treated to strand-separate (e.g., thermally denature) the extension product, and then subjected to conditions whereby the third probe anneals to its target segment, which will comprise at least part of the 3'-end of the segment added to the 3'-end of second probe in the extension reaction and may overlap at least a part of the segment of the extension product which was second probe, and at least the extended second probe is further extended, employing reverse transcriptase activity and the third probe, including its replicase amplifiable segment, as template. Subsequent to the second extension of second probe, the sample is treated as described above, for the embodiment of the invention which utilizes an RNA probe, to substantially eliminate replicase-amplifiable segment of third probe by diminishing the concentration of such segment to an insignificant level before replicase is added to effect amplification. Thus, the solution is subjected to conditions to degrade RNA chemically or enzymatically, as understood in the art, and might be treated further to dilute remaining replicase-amplifiable segment of third probe. After degradation of the RNA and substantial elimination of RNA-degrading conditions, Qβ replicase or another RNA replicase, which recognizes the replicase-amplifiable segment of the RNA probe as a template for autocatalytic replication, is added to the sample and the sample is subjected to conditions whereby the DDRP activity of the replicase catalyzes amplification from the complex, replicase-amplifiable segment of doubly extended second probe. As in other embodiments of the invention, once the DDRP activity-catalyzed amplification has occurred, the amplified material may be detected by suitable means known to those skilled in the art.

As the skilled will understand, target segment(s) is (are) selected so that, in a sample of nucleic acid to which a method of the invention is applied, target segment, or the combination of target segments, required for amplification in accordance with the method of the invention to occur is present in an amount distinguishable from background only if target nucleic acid is present in the sample. Preferably target segment(s) is (are) selected so that the required target segment or combination of target segments is absent from a sample unless target nucleic acid is present.

The present invention is also directed to quantification of the amount of target nucleic acid analyte in a sample. Quantification is accomplished by comparing the amount detected of a first amplified nucleic acid, the amplification of which occurs only if target nucleic acid analyte is present in a sample, with the amount detected of a second amplified nucleic acid, the amplification of which is carried out in parallel with that of the first amplified nucleic acid and occurs on account of the presence in the sample of a preseledted nucleic acid which serves as an internal standard and is present in the sample in a known amount.

The present invention also encompasses a test kit for detection of a specific target nucleic acid analyte in a sample of nucleic acid. The kit comprises one or more nucleic acid probes required for amplification, in accordance with the invention, of a reporter molecule, Qβ replicase or an equivalent enzyme to provide DDRP activity, and other enzymes (if any) required for processing of analyte or probe(s) prior to or simultaneously with amplification catalyzed by the DDRP activity. The kit may also comprise means for detecting reporter nucleic acid produced in the amplification according to the invention, and various components, such as buffers and nucleoside triphosphates, to facilitate carrying out the required hybridizations and enzymatically catalyzed reactions, including autocatalytic replication. A kit may also comprise components required for amplification associated with a pre-selected nucleic acid as an internal standard and detection of product from such amplification, in order to provide for quantification in accordance with the invention of target nucleic acid analyte to be assayed for with the kit. The various components of kits according to the invention may be packaged in a kit in any of a variety of ways, among usually a plurality of vials or other containers, as dictated by factors understood in the art, such as the need to preserve the stability and purity of the components over the shelf-life of the kit, the order in which various components are used in accordance with the invention, convenience in using the kits, convenience and cost in manufacturing the kits, and the like.

Various methods known in the art can be employed to detect reporter molecules provided by an amplification process in accordance with the invention. Thus, the reporter nucleic acid can be reacted with various dyes and the dye detected visually or spectrophotometrically. Alternatively, a ribonucleoside 5'-triphosphate, that is labelled for detection and remains active as a substrate for the Qβ replicase or other replicase catalyzing the amplification, can be employed in the amplification reaction and then signal from the label incorporated into the amplified reporter can be detected directly or, after association of the label with a signal-generating molecule, indirectly. In still another alternative, reporter nucleic acid resulting from amplification can be hybridized with nucleic acid probe that is labelled for detection and signal associated with such probe hybridized to reporter can be detected directly or indirectly.

Among the advantages of the methods of the invention, and kits of the invention for carrying out the methods, is speed. The amplification process of the invention is typically able to produce more than $10^9$ reporter molecules for each target molecule in a sample in about 60 minutes. Further, systems for carrying out the present invention are relatively simple in design and superior to systems which require use of RNA to initiate amplification. The DNA used for this purpose in methods of the present invention is resistant to degradation catalyzed by RNases and provides more synthetic options than their RNA counterparts. Chemically synthesized DNA also provides a cost advantage over RNA. The present invention is especially useful for amplification based on a rare species of nucleic acid present in a mixture of nucleic acids to provide effective detection of the presence, and quantity, of the species.

Target nucleic acid analytes for amplification or detection by the methods of the present invention include, inter alia, nucleic acids characteristic of bacteria, viruses and other vectors of human infectious diseases; genomic nucleic acids comprising abnormalities which underlie human genetic diseases; genomic nucleic acids comprising human cancer genes; nucleic acids used in forensic analyses, paternity testing, compatibility testing for bone marrow transplantations, characterization of plants and animals using restriction fragment length polymorphism, and correlations of improvements through animal-or plant-breeding with genetic changes; and nucleic acids characteristic of organisms which contaminate foods, cosmetics or water or whose presence is diagnostic of environmental conditions in the environment in which the organisms occur.

BRIEF DESCRIPTION OF THE DRAWINGS

FIG. 10 illustrates a partial restriction site and functional map of plasmid pMDV XhoI and the sequence of the HindIII-EcoRI fragment of the plasmid. The HindIII-EcoRI fragment comprises a segment, the strands of which are midivariant DNAs and which comprises an inserted segment with an XhoI site.

DETAILED DESCRIPTION OF THE INVENTION

Figure 1:
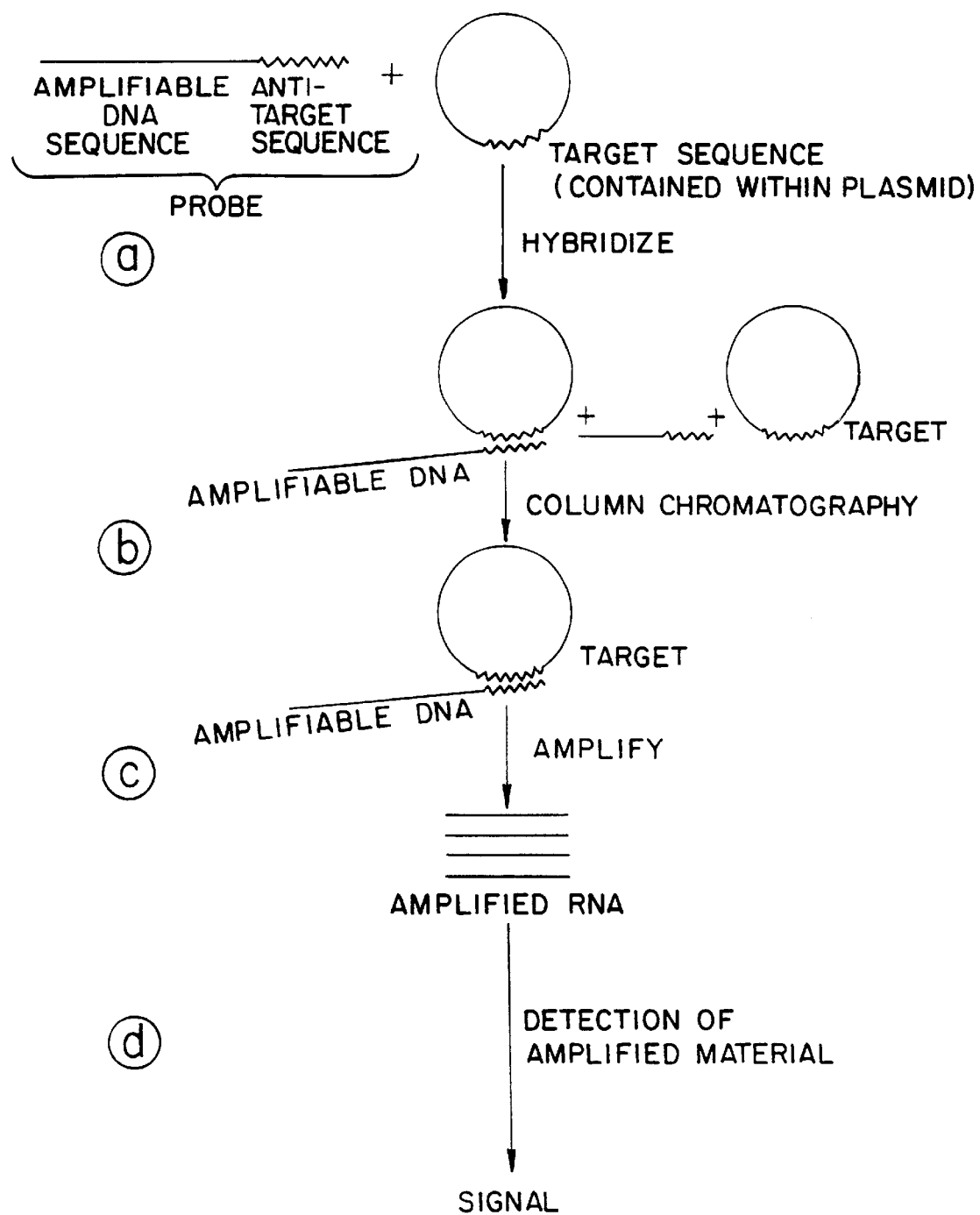
FIG. 1 is a schematic drawing illustrating a method of target nucleic acid segment-directed amplification of a reporter molecule by hybridization of a DNA probe to target sequence (target segment) followed by separation of the hybridized probe from the unhybridized and then amplification of the amplifiable segment of the probe while hybridized to target. As illustrated in the Figure, the amplified product (RNA) may be detected.

The present invention rests on the surprising and unexpected discovery that an RNA replicase, such as Qβ replicase, has DDRP activity with a complex template which comprises a 2'-deoxyribonucleotide or an analog thereof in place of a ribonucleotide but otherwise has the sequence of an RNA which is autocatalytically replicatable by the replicase. As indicated hereinabove, the invention encompasses numerous practical applications of this discovery, in nucleic acid segment amplification, target nucleic acid detection, and other fields.

Thus, in one of its aspects, the invention entails a method of amplifying a complex nucleic acid segment, which comprises a 2'-deoxyribonucleotide or an analog thereof, and has the sequence of an RNA which is autocatalytically replicatable by an RNA replicase, which method comprises subjecting a sample which comprises said segment to conditions effective for autocatalytic replication by said replicase.

"Complex nucleic acid segment" is defined above.

Conditions effective for autocatalytic replication by an RNA replicase, such as Qβ replicase, are well known or easily ascertained by the skilled. Such conditions entail providing in the aqueous solution, in which the replicase is present, conditions of pH, ionic strength, temperature, and concentration of $Mg^{+2}$ at which the replicase is active in catalyzing autocatalytic replication and providing as well in said solution the four ribonucleoside 5'-triphosphates (hereinafter referred to simply as "ribonucleoside triphosphates"), which RNA replicases employ as substrates in catalyzing the process. Examples of such conditions are provided in the examples hereinbelow. "Autocatalytic replication" is, as understood in the art, a process catalyzed by an RNA replicase in which an RNA template is employed as a substrate, along with the four ribonucleoside triphosphates, to make an RNA with the sequence complementary to that of the template. The RNA that is made is also a template for the process. (Certain ribonucleoside triphosphate analogs, such as rTTP or UTP with the 5-carbon of the uracil linked to biotin (see, e.g., Langer et al., Proc. Natl. Acad. Sci. (1981) 78, 6633) can be employed together with the four standard ribonucleoside triphosphates in autocatalytic replication.) Usually, in a template for DDRP activity of a replicase in accordance with the invention, fewer than 1 in 10 nucleotides will be a 2'-deoxyribonucleotide analog or a ribonucleotide analog. Further, in carrying out DDRP activity on a complex template and autocatalytic replication of the polynucleotide resulting from the DDRP activity, usually less than about 10 mole % of substrate for the replicase for incorporation into the product of the autocatalytic replication will be analogs of ribonucleoside triphosphates and, more typically, such analogs will be of only one of the four ribonucleoside triphosphates and will be present at less than about 10 mole % of that particular ribonucleoside triphosphate. Preferably, only 2'-deoxyribonucleotides and ribonucleotides will be present in templates for DDRP activity of a replicase and only ribonucleoside triphosphates will be used as substrates for DDRP activity and autocatalytic replication.

As indicated above, divalent transition metal ions, such as $Mn^{+2}$, $Co^{+2}$, or $Zn^{+2}$, may also be present to advantage in reaction media in which amplification via DDRP activity in accordance with the invention is carried out. These ions, as well as the $Mg^{+2}$ required for replicase activity, are provided as any salt, which is sufficiently soluble in the solution to achieve the desired metal ion concentration and the anion of which does not inactivate the replicase. Suitable salts are well known to the skilled and include the halide salts (e.g., chloride, bromide), the carbonates, the sulfates, the nitrates, and the like.

In another aspect, the invention entails applying the amplification process of the invention in a target-dependent manner. Thus, the invention entails a method of treating a sample comprising nucleic acid to make a reporter RNA, which is autocatalytically replicatable by an RNA replicase, only if the sample comprises a pre-selected target nucleic acid segment, which method comprises (a) treating a first aliquot of the sample of nucleic acid with one or more nucleic acid probes, each of which is capable of hybridizing to a subsegment of the target segment or the complement of a subsegment of the target segment, provided that at least one of the probes is capable of hybridizing to a subsegment of the target segment, and which (i) if one probe is employed in the method, said probe is, or is capable of being processed to make, a complex nucleic acid segment comprising a 2'-deoxyribonucleotide or an analog thereof and having the sequence of the reporter RNA or the complement of the reporter RNA, or (ii) if more than one probe is employed in the method, said probes are capable of being processed to make a complex or broken complex nucleic acid segment comprising a 2'-deoxyribonucleotide or an analog thereof and having the sequence of the reporter RNA or the complement of the reporter RNA; (b) processing said first aliquot, including said probe or probes, to prepare a second aliquot wherein (i) said complex or broken complex nucleic acid segment comprising a 2'-deoxyribonucleotide or an analog thereof and having the sequence of the reporter RNA or the complement thereof is made, if not provided as part of a single probe, and remains in an amount that is significant in view of step (c) only if target segment is present in the sample, and (ii) any nucleic acid segment, which lacks 2'-deoxyribonucleotides and analogs thereof but is a template for synthesis of reporter RNA or the complement thereof by said RNA replicase, is reduced to an amount that is insignificant in view of step (c); and (c) subjecting the second aliquot, or a third aliquot taken from said second aliquot, to conditions effective for autocatalytic replication in the presence of said replicase.

Several different embodiments of this target-dependent amplification method of the invention are described elsewhere herein. The method requires production of reporter RNA (or its complement) via the DDRP activity of a replicase. Because RNA (or RNA including ribonucleotide analogs) made by DDRP activity is autocatalytically replicated, to provide the RNA that is complementary in sequence, the "reporter RNA" can be selected, arbitrarily, to be either the RNA with the sequence complementary to that of the complex segment which is the template for the DDRP activity or the complement of that RNA. To insure that the target-dependent amplification process, to the extent it is observable, is due to the DDRP activity of a replicase, which acts on a complex nucleic acid segment comprising a 2'-deoxyribonucleotide or analog thereof, any probe employed in the process, which provides a segment which has the sequence of the reporter RNA or its complement, does not comprise a 2'-deoxyribonucleotide or analog thereof, and is a template for the replicase (e.g., an RNA probe with such a segment) must be reduced to a level (e.g., concentration) that is insignificant, given the amplification process that is carried out on the complex segment comprising a 2'-deoxyribonucleotide or analog thereof, before that amplification process is carried out. A level that is "insignificant" will vary depending on the details of the amplification process, including its duration and the rates of autocatalytic replication of reporter RNA and its complement and DDRP activity using the complex segment which is the template for such activity. A level is "insignificant" if it does not result in a measurable amount of reporter RNA when the process is carried out with a sample known to lack target segment. Preferably, of course, the level will be zero. Generally this level and, in any case, levels that are clearly "insignificant" are easily achieved, as described elsewhere herein, by combining treatment with base (which, as well known, degrades RNA much more rapidly than DNA) or a ribonuclease with dilution. (As a practical matter, the probes that need to be reduced to an "insignificant" level are either RNAs or comprise enough ribonucleotides to be susceptible to degradation by ribonucleases.)

"Conditions effective for autocatalytic replication" require that conditions not prevail which entail degradation at a substantial rate of RNA, which is made by the DDRP activity and in the autocatalytic replication. Thus, if ribonucleases might be present in step (c) of the target-dependent amplification process of the invention at a level which might cause problematic degradation of reporter RNA, ribonuclease inhibitors should be employed to block such degradation. Such inhibitors might be employed in step (c) of the process if, in step (b), one or more ribonucleases were employed to degrade probe that is a template for synthesis of reporter RNA or complement thereof but is not a complex segment comprising a 2'-deoxyribonucleotide or analog thereof.

Typically, one two or three probes, each of which is a DNA or an RNA, are employed in the target-dependent amplification process of the invention for each target segment. If one probe, which is a DNA or otherwise is a complex substrate comprising a 2'-deoxyribonucleotide or analog thereof, is used, such a substrate does not need to be made but the sample with the probe is processed, by methods well known to the art, so that probe will remain at a significant level (e.g., concentration) only if target segment is present. By "significant" level is meant a level that, given the details of the process of amplification via DDRP activity and autocatalytic replication in part (c) of the process, yields an amount of reporter RNA that is observable (detectable above "background"). If a single RNA probe, or more than one probe, are used, additional processing is required, as described in more detail elsewhere in the present specification, to make a complex segment, that comprises a 2'-deoxyribonucleotide or analog thereof and that is a substrate for DDRP activity of the replicase, and have that segment remain at a. significant level only if target segment is present and to reduce RNA probe (if any) to an insignificant level.

In still a further aspect, the invention entails a method of assaying a sample for the presence of a target nucleic acid analyte which method comprises carrying out with the sample target nucleic acid-mediated amplification, in accordance with the invention, of a reporter nucleic acid followed by assay of the sample for the presence of a nucleic acid with the sequence of reporter nucleic acid (or its complement). The "reporter nucleic acid" is generally reporter RNA.

Thus, the invention entails a method of detecting the presence of a target nucleic acid analyte, comprising a pre-selected target segment, in a test sample thought to contain said target nucleic acid, said method comprising treating said sample of nucleic acid to make a reporter RNA, which is autocatalytically replicatable by an RNA replicase, only if the sample comprises said pre-selected target segment, and assaying for any reporter RNA so made, said treating comprising (a) treating a first aliquot of the sample of nucleic acid with one or more nucleic acid probes, each of which is capable of hybridizing to a subsegment of the target segment or the complement of a subsegment of the target segment, provided that at least one of the probes is capable of hybridizing to a subsegment of the target segment, and which (i) if one probe is employed in the method, said probe is, or is capable of being processed to make, a complex nucleic acid segment comprising a 2'-deoxyribonucleotide or an analog thereof and having the sequence of the reporter RNA or the complement of the reporter RNA, or (ii) if more than one probe is employed in the method, said probes are capable of being processed to make a complex or broken complex nucleic acid segment comprising a 2'-deoxyribonucleotide or an analog thereof and having the sequence of the reporter RNA or the complement of the reporter RNA; (b) processing said first aliquot, including said probe or probes, to prepare a second aliquot wherein (i) said complex or broken complex nucleic acid segment comprising a 2'-deoxyribonucleotide or an analog thereof and having the sequence of the reporter RNA or the complement thereof is made, if not provided as part of a single probe, and remains in an amount that is significant in view of step (c) only if target segment is present in the sample, and (ii) any nucleic acid segment, which lacks 2'-deoxyribonucleotides and analogs thereof but is a template for synthesis of reporter RNA or the complement thereof by said RNA replicase, is reduced to an amount that is insignificant in view of step (c); and (c) subjecting the second aliquot, or a third aliquot taken from said second aliquot, to conditions effective for autocatalytic replication in the presence of said replicase.

Any of numerous methods can be employed to assay for reporter RNA (or its complement). In situations where the mass of reporter RNA and its complement, if made, will be substantial fraction of the mass of nucleic acid present after the amplification, a nucleic acid-staining dye can simply be added to an aliquot of sample in which the amplification was carried out and the aliquot can be visualized to see whether staining has occurred. Staining will occur and be observed only if target nucleic acid was present to lead to production of reporter RNA. Situations in which this simple staining technique can be applied include those where, after amplification, the stained reporter RNA and its complement are visible in an aliquot of sample and the mass of such stained reporter RNA and complement exceeds by a factor of at least about two the mass of other nucleic acid present in the sample after the amplification.

In situations where the amount of reporter RNA and its complement formed in the amplification process is too low to allow simple staining to be used to detect whether target nucleic acid was present in a sample, the nucleic acid of an aliquot of a sample, after the amplification process is carried out with the sample, can be separated by size, e.g., electrophoretically, and then stained. Production in the amplification process of nucleic acid of the size of reporter RNA and its complement, as detected by observing stained nucleic acid of that size in the size-separated nucleic acid, indicates that target nucleic acid was present in the sample of nucleic acid being analyzed.

Alternatively, reporter RNA and its complement, that are made during the amplification process if target analyte is present in a sample being assayed, can be labelled in the course of the amplification, e.g., by employing some $^{32}$P-labelled ribonucleoside triphosphate or biotinylated UTP in the substrate for the replicase, and then the labelled reporter RNA or its complement, if they are made, can be detected via the label as understood in the art. Prior to the detection process, labelled reporter and its complement (if any) must be separated from labelled ribonucleoside triphosphate that was not incorporated into RNA during the amplification process, e.g., chromatographically, by hybridization of reporter RNA or complement thereof to latex beads or magnetic particles to which single-stranded nucleic acids with sequences complementary to that of a segment of reporter or its complement are covalently attached.

Still other methods of assaying for production of reporter RNA or its complement are by nucleic acid probe hybridization assays for either. In these assays, a nucleic acid that is labeled for detection and that is capable of hybridizing to the reporter RNA or its complement is employed as understood in the art.

Finally, because synthesis of reporter RNA and its complement in the amplification process consumes ribonucleoside triphosphates or analogs thereof, the concentration of such a compound in a solution in which amplification will be occurring, if target analyte was present in a sample being assayed, can be monitored to determine whether amplification did occur. The depletion of such a compound indicates that amplification has occurred. One such compound whose depletion can be monitored readily is ATP; such monitoring can be carried out by measuring, as understood in the art, bioluminescence as catalyzed by a luciferase, e.g. from a beetle such as *P. pyralis*.

The invention also involves kits for carrying out the various methods of the invention, particularly the target-dependent amplification methods and the methods for detecting nucleic acid analyte.

Thus, the invention entails a kit for amplification, dependent on the presence in a sample of nucleic acid of a nucleic acid comprising a pre-selected target segment, of a reporter RNA, which is autocatalytically replicatable by an RNA replicase, said kit comprising, packaged together, a replicase-holding container and one or more probe-holding containers; said replicase-holding container holding a replicase solution which comprises an RNA replicase for which the reporter RNA is a template for autocatalytic replication; and said probe-holding container, if one, or each of said probe-holding containers, if more than one, holding a probe solution comprising one or more of the nucleic acid probes required for said amplification ("required probes"), provided that all of said required probes are held in the one or more probe-holding containers which the kit comprises; said required probe or, if more than one, each of said required probes being capable of hybridizing to a subsegment of the target segment or the complement of a subsegment of the target segment, provided that: (i) at least one of the probes is capable of hybridizing to a subsegment of the target segment; (ii) if there is one required probe, said probe is, or is capable of being processed to make, a complex nucleic acid segment comprising a 2'-deoxyribonucleotide or an analog thereof and having the sequence of the reporter RNA or the complement of the reporter RNA; (iii) if there is more than one required probe, said probes are capable of being processed to make a complex or broken complex nucleic acid segment comprising a 2'-deoxyribonucleotide or an analog thereof and having the sequence of the reporter RNA or the complement of the reporter RNA. These kits of the invention may comprises additionally, packaged with the replicase-holding container and the one or more probe-holding containers, one or more enzyme-holding containers, each of which holds a solution of an enzyme used in any processing of probes necessary to make a complex or broken complex nucleic acid segment comprising a 2'-deoxyribonucleotide or an analog thereof and having. the sequence of the reporter RNA or the complement of the reporter RNA.

These kits of the invention may be test kits for detecting the presence of a target nucleic acid analyte, comprising a pre-selected target segment, in a test sample thought to contain said analyte. Such test kits comprise additionally reagents for rendering detectable reporter RNA or complement thereof produced in the amplification carried out with the components of the kit on an aliquot of the test sample if said sample comprises said analyte. In the test kits, such reagents will be held in detection-reagent-holding containers that are packaged together with the replicase-holding, probe-holding and any enzyme-holding containers. Such reagents, which might be included in a test kit, include, for example, a solution of a dye to stain nucleic acid, a solution of a nucleic acid probe that is labeled for detection and that is capable of hybridizing to reporter RNA or complement thereof, or a solution of a beetle luciferase.

"Autocatalytic replication" and "autocatalytically replicatable" are terms known in the art. See, e.g., Chu, et al., PCT Patent Publication No. WO 87/06270, and references cited therein; Kramer, et al., U.S. Pat. No. 4,786,600. Under conditions where the concentration of autocatalytically replicatable template RNA does not exceed that of the replicase catalyzing autocatalytic replication, the process is an exponential one.

For purposes of the present invention, the term "connector sequence" or "connector segment" is intended to mean a nucleic acid segment which is not all or part of an amplifiable (i.e., autocatalytically replicatable) segment and not an anti-target segment, but rather is a segment that joins two of such segments in a probe.

The term "target nucleic acid," as used herein, refers to the specific nucleic acid analyte to initiate a target-dependent amplification in accordance with the invention or to be detected in a sample comprising nucleic acid and suspected of containing the nucleic acid analyte. A target nucleic acid will comprise a "target segment," to which probes of the invention hybridize in processes of the invention.

The term "anti-target nucleic acid sequence," "anti-target sequence," "anti-target" or "anti-target segment," as used herein, is intended to mean the segment of a nucleic acid probe with a sequence (of bases) which is at least partially (and preferably exactly) complementary to the sequence (of bases) of the nucleic acid segment ("target segment") to which the probe is intended to hybridize in processes of the invention. Hybridization between anti-target segments and their corresponding target segments provides specificity for target nucleic acid in methods of the invention.

To effect hybridizations with the intended specificity in carrying out the methods of the present invention generally requires that anti-target segments have at least six, and preferably at least 12, and more preferably about 20–about 35 nucleotides. Factors which affect specificity of hybridizations are well understood by the skilled and include, in addition to the lengths of the hybridizing segments, the complexity of the mixtures of nucleic acids in which the hybridization are carried out and the stringency at which the hybridizations are carried out. For a mixture of nucleic acid of a given complexity, the skilled can manipulate anti-target segment length, stringency, and selection of sequence of target segment to achieve the required specificity.

The term "probe" or "nucleic acid probe" as used herein refers to a nucleic acid which is a DNA, an RNA, or a chimeric nucleic acid and which comprises an anti-target segment. A probe may be made synthetically, as in an automated synthesizer, or derived from cellular or viral substituents. It will be single-stranded, but may be accompanied by its complementary strand (or a segment thereof). A probe must comprise an anti-target segment, However, as indicated above, in some embodiments of the invention a probe may be employed which is intended to hybridize to a segment which is complementary in sequence to a segment of target nucleic acid; the anti-target segment of such a probe will be a "target-like" segment and, as such, will have the same, or nearly the same, sequence as a segment of target nucleic acid.

The term "reporter molecule" or "reporter nucleic acid" as used herein is intended to mean a nucleic acid generated in an amplification process of the invention, which depends on the presence in a sample of a target nucleic acid. "Reporter RNA" may consist of the four standard ribonucleotides (unlabelled or labelled with a radioactive isotope (e.g., $^{32}P$) of an element which occurs normally in the ribonucleotide) or, as described elsewhere herein, may include various ribonucleotide analogs which function as substrates for an RNA replicase in autocatalytic replication and which, if present in an RNA with the sequence of a template for autocatalytic replication by an RNA replicase, do not block the replicase from replicating the template.

"Amplification of a reporter nucleic acid" can mean either (i) replication by DDRP activity of a replicase of a complex reporter segment which comprises a 2'-deoxyribo-nucleotide or an analog thereof into another reporter of complementary sequence which is completely an RNA (or which may comprise a ribonucleotide analog (e.g. uridine linked through the 5-position of the uracil to a biotin moiety) the 5'-triphosphate of which is a substrate for the replicase and which, in the RNA, does not block the RNA's functioning as a template for autocatalytic replication by the replicase) and which is a template for autocatalytic replication by the replicase followed by autocatalytic replication of said autocatalytically replicatable reporter or (ii) simply autocatalytic replication of an autocatalytically replicatable reporter which is an RNA or an RNA which comprises a ribonucleotide analog as just described.

Either the presence or absence of reporter molecules, or the amount produced, can be used as an indicator of the presence (or absence, respectively) of the target analyte in a sample. A "reporter molecule" will have a "reporter sequence," through which the reporter molecule may be detected and which may be the sequence of the entire molecule or a segment thereof.

"Amplification" of a nucleic acid or segment thereof means the process of making multiple copies of a nucleic acid which has the same sequence as the nucleic acid (or segment) being amplified. The term "segment-directed amplification" or "target-directed amplification" as used herein is intended to mean a replicase-mediated process whereby each target nucleic acid molecule (or, more precisely, target segment(s), selected to be uniquely characteristic of target nucleic acid) is used to initiate production of multiple reporter molecules.

The term "amplifiable sequence" or "amplifiable nucleic acid sequence" is intended to mean the sequence of an RNA which is autocatalytically replicatable by an RNA replicase. Thus, reference is sometimes made to a "replicase-amplifiable" sequence or segment.

A "segment" of a nucleic acid strand is the entire nucleic acid strand or any part thereof with a continuous sequence of at least two nucleotides (or nucleotide analogs) as in the nucleic acid strand. A "subsegment" of a segment of a nucleic acid strand is the entire segment or any part of the segment with a continuous sequence of at least two nucleotides (or nucleotide analogs) as in the segment.

An "aliquot" of a sample or, more typically, a solution is, as understood by the skilled, a part of the sample or solution which will have intrinsic properties (e.g., composition, concentrations of constituents) that are indistinguishable from those of the sample or solution as a whole.

The discovery underlying the invention is that a nucleic acid which comprises a 2'-deoxyribonucleotide or analog thereof but has a complex, amplifiable sequence for an RNA replicase functions as a template for synthesis, catalyzed by the replicase, of an RNA, which has the complementary, also amplifiable sequence, and which, therefore, is autocatalytically replicatable. Thus, surprisingly and advantageously, a complex segment comprising a 2'-deoxyribonucleotide or an analog thereof and having an amplifiable sequence can be used to make an autocatalytically replicatable RNA and, thereby, initiate the process of autocatalytic replication.

By reference herein to a nucleic acid which is an RNA is meant a nucleic acid consisting of only one or more of the four standard ribonucleotides, adenosine monophosphate (A or rA), uridine monophosphate (U), guanosine monophosphate (G or rG) and cytidine monophosphate (C or rC). By reference herein to a "ribonucleotide," without further qualification, is mean on of the four standard ribonucleotides. By reference herein to a nucleic acid which is a DNA is meant a nucleic acid consisting of only one or more of the four standard 2'-deoxyribonucleotides, 2'-deoxyadenosine monophosphate (A or dA), 2'-deoxythymidine monophosphate (T), 2'-deoxyguanosine monophosphate (G or dG) and 2'-deoxycytidine monophosphate (C or dC). A "nucleotide" without further qualification means a 2'-deoxyribonucleotide, a 2'-deoxyribonucleotide analog, a ribonucleotide, or ribonucleotide analog. A "nucleic acid," without further qualification, means a double-stranded or single-stranded oligonucleotide or polynucleotide. A "chimeric" nucleic acid is a single-stranded nucleic acid in which some of the nucleotides are ribonucleotides or ribonucleotide analogs and some are 2'-deoxyribonucleotides or 2'-deoxyribonucleotide analogs. A "non-analog" chimeric nucleic acid is a chimeric nucleic acid which consists of ribonucleotide(s).and 2'-deoxyribonucleotide(s) and, as such, includes analogs of neither. An "hybrid" nucleic acid is a double-stranded, or partially double-stranded, nucleic acid, in which one of the strands is DNA and the other is RNA or chimeric or one of the strands is RNA and the other is DNA or chimeric. The "nucleotide" at the 5'-end of a nucleic acid need not necessarily have a single 5'-phosphate; it might have, for example, a 5'-triphosphate or a 5'-hydroxyl. Similarly, the "nucleotide" at the 3'-end of a nucleic acid need not necessarily have a 3'-hydroxyl; it might for example, have a 3'-phosphate.

2'-deoxyribonucleotide analogs, which may be included in complex nucleic acid templates for amplification via the DDRP activity of a RNA replicase in accordance with the instant invention, are described above.

Among such 2'-deoxyribonucleotide analogs are "(2'-deoxyribonucleotide) phosphate analogs," by which is meant analogs wherein the phosphate of the corresponding 2'-deoxyribonucleotide is replaced with a phosphate analog such as an alkylphosphonate (wherein the alkyl group may be, for example, a methyl, ethyl, n-propyl, or i-propyl), a phosphorothioate, a phosphotriester, or a phosphoramidate.

Thus, analogs of 2'-deoxyribonucleotides which may occur in complex templates for DDRP activity of RNA replicases in accordance with the invention include 2'-deoxyriboalkylphosphonates (see Blake et al., Biochemistry (1985) 24, 6139), 2'-deoxyribophosphorothioates (see Froehler, Tetrahedron Lett. (1986) 27, 5575), 2'-deoxyribophosphotriesters (see Blackburtn et al., J. Chem. Soc. (C) (1966), 239), and 2'-deoxyribophosphoramidates (see Zwierzak, Synthesis (1975), 507).

A "ribonucleotide analog" is a ribonucleotide wherein the base is derivatized at a carbon or amino nitrogen or wherein the phosphate is replaced with a phosphate analog (a "(ribonucleotide) phosphate analog"). A ribonucleotide analog in a complex segment which is a template for the DDRP activity of an RNA replicase or in a polyribonucleotide made from such a complex segment on the basis of such activity is recognized by the replicase, in such a complex segment of polyribonucleotide, to place the ribonucleotide with the base, that is complementary to that of the analog, in the corresponding position of the autocatalytically replicatable RNA made from the complex segment or polyribonucleotide. Among ribonucleotide analogs are rT and other derivatives of U, wherein the uracil is derivatized at the 5-carbon (e.g., through a linker to biotin) and various phosphate analogs corresponding to phosphate analogs of the 2'-deoxyribonucleotides (see listing above of 2'-deoxyribonucleotide phosphate analogs).

A 2'-deoxyribonucleotide, 2'-deoxyribonucleoside 5'-triphosphate (hereinafter referred to simply as a "2'-deoxyribonucleoside triphosphate"), ribonucleotide or ribonucleoside triphosphate which is changed only by changing the percentages of the various isotopes of an atom is not considered an "analog."

The term "amplifiable probe" is intended to mean a nucleic acid which has the characteristics of a probe and has an amplifiable sequence.

In accordance with the terminology used in the present specification, two single-stranded nucleic acids will have the "same" sequence, even if both of them are chimeric, or one of them is an RNA and the other a DNA or chimeric, or one of them is a DNA and the other an RNA or chimeric, as long as both have the same number of nucleotides and the sequence of bases on the nucleotides is the same in both. For purposes of determining whether two nucleic acid sequences are the "same," a base derivatized at one of its atoms (other than the nitrogen bonded to the ribose) is considered to be the same as the underivatized base. Thus, for example, an RNA and a DNA will have the same sequence if they have the same number of bases and the sequence of bases is the same in both, with each uracil in the RNA corresponding to a thymine in the DNA.

The term "silent sequence" or "silent segment" in reference to amplification is intended to mean a nucleic acid segment which, in a first nucleic acid, is not amplifiable but which, in combination with other segment(s) in a second nucleic acid made with the first nucleic acid, is part of an amplifiable segment.

The term "Qβ replicase or its functional equivalent" as used herein is intended to mean an RNA replicase which catalyzes autocatalytic replication of certain RNAs as well as, in accordance with the discovery underlying the present invention, synthesis of RNAs using as templates DNAs and chimeric nucleic acids with the sequences of RNAs that are autocatalytically replicatahle by the replicase. For examples of such replicases, reference is made to PCT Patent Publication No. WO 88/10315 to Gingeras, et al., PCT Patent Publication No. WO 87/06270 to Chu, et al., Blumenthal and Carmichael (1979) Ann. Rev. Biochem., 48:525–548, and Miyake et al., (1971) Proc. Natl. Acad. Sci. (USA) 68, 2022–2024, as well as to references cited in these publications. Examples of such replicases that are useful in the present invention include the Qβ replicase, those encoded by the genomes of bacteriophages FI, f2, GA, MS2, R17, SD, SP, ST, VK, and ZR, as well as replicases of plant RNA viruses such as that of brome mosaic virus (BMV). Among the bacteriophage replicases, for example, there is interchangeability of templates for autocatalytic replication.

The skilled understand that there are many types of RNAs that are autocatalytically replicatable by Qβ replicase and other RNA replicases. Thus, among others, there are many so-called nanovariant RNAs and many so-called midivariant RNAs. See, e.g., Chu, et al., PCT Patent Publication No. WO 87/06270 and references cited therein. DNAs, and other nucleic acid segments comprising a 2'-deoxyribonucleotide or analog thereof, and corresponding to all of these RNAs are amplifiable via the DDRP activity of RITA replicases. In the present application, nvDNA, unless otherwise qualified, refers to a specific DNA, namely the double-stranded DNA, one strand of which (referred to as nv(+)DNA) has the same sequence as the nanovariant(+) RNA (nv(+)RNA) taught by Schaffner, et al., 1977, supra, and the other strand of which, referred to as nv(−)DNA, has the exactly complementary sequence. See SEQ ID NO: 1 and SEQ ID NO: 6 for the sequences of nv(+)DNA and nv(−)DNA, respectively. Examples of other nanovariant DNAs are given in Table 1 of Example 3. Similarly, mdvDNA, unless otherwise qualified, refers to the double-stranded DNA with the sequence shown at SEQ ID NO: 23, one strand of which is referred to as mdv(+)DNA, because it has the sequence of a midivariant(+) RNA, and the other strand of which, with the complementary sequence, is referred to as mdv(−)DNA, because it has the sequence of the corresponding midivariant (−) RNA. MdvDNA is a "recombinant" midivariant DNA, as the corresponding RNA was made by inserting, using in vitro "gene-splicing" techniques with various enzymes including restriction endonucleases, an RNA segment (corresponding to bases 66–75 in SEQ ID NO: 23) into a midivariant RNA that is naturally occurring or arose in vitro in the course of autocatalytic replication by Qβ replicase from a naturally occurring RNA template for autocatalytic replication by that enzyme. See Kramer, et al., U.S. Pat. No. 4,786,600. "Nvplasmid" means a plasmid, such as pNV-1-3-4, which comprises nvDNA as a segment. "Nanovariant plasmid" means a plasmid which comprises a nanovariant DNA as a segment. "Mdvplasmid" means a plasmid, such as pMDV XhoI, which comprises mdvDNA as a segment. "Midivariant plasmid" means a plasinid which comprises a midivariant DNA as a segment.

The term "oligonucleotide primer" as used herein is intended to include primers, whether occurring naturally as in a purified restriction digest or produced synthetically, as with a DNA synthesizer, which are capable of priming DNA synthesis when placed under conditions in which synthesis of a primer extension product, which is complementary to a nucleic acid template strand, is induced, i.e., in the presence of 2'-deoxyribonucleotides or certain analogs thereof, as understood in the art, and an enzyme with DNA polymerase activity and at a suitable temperature, pH and stringency for hybridization of primer to template to occur and the enzyme to be active in catalyzing DNA synthesis. The primer is-provided in single-stranded form but may alternatively be doubled-stranded. If double-stranded, the primer is first treated to separate its strands before being hybridized to nucleic acid strand template to initiate preparation of extension products. The primer must be sufficiently long to hybridize to template with sufficient stability to prime the synthesis of extension products in the presence of the enzyme providing DNA polymerase activity. A primer also may provide specificity by hybridizing specifically to a 3'-end of a target segment (or the complement thereof). The exact length of a primer will depend on many factors, including temperature, stringency, and complexity of the target sequence. An oligonucleotide primer typically contains 20–35 nucleotides, although it may contain fewer (down to about 6) or more nucleotides in the segment intended to hybridize with template. Shorter primer molecules generally require lower stringency (e.g., cooler temperatures at constant pH, ionic strength, and other stringency-determining factors) to form sufficiently stable hybrid complexes with the template and tend therefore to be somewhat less specific with respect to segments to which they hybridize and initiate synthesis.

Replicase Enzyme Activity

The present invention employs the use of RNA replicases, such as that of RNA bacteriophage Qβ. The present invention employs a novel activity of the replicases, i.e., DNA-dependent RNA polymerase activity. The activity produces RNA copies from complex, DNA or chimeric nucleic acid substrates which have sequences of autocatalytically replicatable RNAs for the replicase. The definition of "complex" with reference to substrates for RNA replicases is provided supra. The RNA copies provided by the DDRP activity are autocatalytically replicated by the same replicase (or another that recognizes the RNA as a template for autocatalytic replication). The substrate for the Qβ replicase, for example, can be any amplifiable DNA, e.g., nanovariant DNAs, midivariant DNAs, minivariant DNAS, other variants including those to which names for the corresponding autocatalytically replicatable RNAs have not been assigned, or autocatalytically replicatable mutants thereof.

Prior to this invention, it had not been appreciated that RNA replicases manifest a DNA-dependent RNA polymerase activity capable of using complex DNAs and chimeric nucleic acids as templates for making RNAs of complementary sequence that are autocatalytically replicatable. Indeed, it has been reported that DNAs with complex sequences but having terminal polydeoxycytidine were not active as templates for autocatalytic replication by Qβ replicase. Feix, G. and H. Sano (1976) FEBS Letters, 63:201–204.

Further, Feix and Sano, supra, reported that the DDRP activity they observed, narrowly limited with respect to template, was not increased by the replacement of $Mg^{+2}$ with $Mn^{+2}$ in the reaction medium. However, in another aspect of the present invention, it has been found surprisingly that amplification of DNA and chimeric substrates, via the DDRP activity of RNA replicases, although apparently requiring $Mg^{+2}$, is enhanced in the presence of divalent transition metal cations, such as $Mn^{+2}$, $Co^{+2}$, or $Zn^{+2}$, in the reaction media at above about 0.5 mM, typically at no more than about 5 mM and preferably at about 1 mM.

Reference herein to "about" with respect to a concentration or an amount has the meaning ascribed to that term by practitioners in the molecular biological and biochemical arts and, as such, generally means the specified concentration or amount ±10%.

Templates

The DDRP activity of Qβ replicase and other RNA replicases is active on any complex DNA or chimeric nucleic acid segment which has the sequence of an RNA that is autocatalytically replicatable by the replicase. It has been discovered, in connection with the present invention, that the replicases are remarkably versatile in their capability to "identify" a nucleic acid segment with a sequence of an RNA that is autocatalytically replicatable with the replicase. Thus, such a complex DNA or chimeric segment can be free, in single-stranded form, with no nucleotides joined to either of its ends. Alternatively, such a complex segment can be single-stranded with nucleotides, which are not copied by the replicase into the RNA made with the DDRP activity, added at either or both ends. Still further, the complex segment can be all or part of one strand of a double-stranded or partially double-stranded nucleic acid, including an hybrid nucleic acid, a nucleic acid in which the two strands are not exactly complementary in sequence, and a nucleic acid in which there may be gaps (one or more nucleotides missing) or breaks (a severed phosphodiester bond but no nucleotides missing) in one or both strands. Indeed, a plurality of segments which, if covalently joined together, would form a complex segment that is a template for the DDRP activity of an RNA replicase, will function as such a complex segment, even if not covalently joined together, provided that the plurality of segments is hybridized immediately adjacent one another (i.e., with only breaks but no gaps between them) in the same order the segments would have in the complex segment, on a nucleic acid strand. Such a plurality of segments is referred to herein as a "broken complex segment." The "sequence" of a broken complex segment is the sequence of the complex segment formed by closing the breaks between the segments of the broken complex segment. Because the hybridization of the plurality of segments (preferably two) which constitute a broken complex segment needs to be sufficiently stable, each of the plurality of segments must have at least about 6, and typically at least about 10, bases in a segment complementary in sequence to a segment of the other strand to which the plurality of segments hybridizes. The segment of the plurality at the 3'-end of the broken complex segment and the segment of the plurality at the 5'-end of the broken complex segment need not be completely hybridized to the other strand; only a subsegment at the 5'-end of the segment of the plurality at the 3'-end and a subsegment at the 3'-end of the segment of the plurality at the 5'-end need be hybridized to the other strand. If, in the strand other than that with a first complex segment or broken complex segment, which is a template for autocatalytic replication by a RNA replicase, there is a second complex segment exactly complementary in sequence to that of the first complex segment or broken complex segment, the second complex segment will also be a template for DDRP activity of the replicase. Whether single-stranded, double-stranded or partially double-stranded, the nucleic acid in which a complex segment, with the sequence of an RNA that is autocatalytically replicatable by an RNA replicase, may be embedded and be operable as a template for the DDRP activity of the replicase can be in any physical form, linear (single-stranded or double-stranded), closed circular, super-coiled, or the like. Thus, the complex DNA or complex segment that is a template for the DDRP activity of an RNA replicase can be a segment of a plasmid, including a relaxed or a super-coiled plasmid.

It has been discovered, then, in connection with the present invention, that a template in accordance with the invention for amplification with an RNA replicase can be provided to a sample as a pre-formed, single nucleic acid, which comprises a complex segment which has the sequence of an RNA that is autocatalytically replicatable by the replicase, or as one or more nucleic acids which can be processed or reacted in the sample to provide a nucleic acid which comprises a complex or broken complex nucleic acid segment which has the sequence of an RNA that is autocatalytically replicatable by the replicase.

The present invention provides a simple, straight-forward method for identifying RNAS, including the many already known to the art, as described above, which are templates for autocatalytic replication by Qβ replicase or other RNA replicases. Thus, employing methods well known to the skilled, a DNA, most conveniently a plasmid or other vehicle suitable for conveniently making significant amounts of DNA by cloning, is made which comprises a segment with the sequence of an RNA known to be autocatalytically replicatable by an RNA replicase. As discovered in connection with this invention, both strands of this segment will be amplifiable by the replicase, beginning with the DDRP activity of the replicase. This segment can then be changed by any method known in the art, to delete, add, or change bases, and plasmid DNA with the changed segment exposed to the replicase under conditions, such as those described herein, which will result in amplification if the DNA of the modified segment has the sequence of an RNA that is autocatalytically replicatable by the replicase. Detection of amplification can also be carried out as described herein.

For example, examples 3, 4, 5 and 8 below show segments with sequences modified form that of nv(+)RNA or nv(−)RNA which retain autocatalytic replicatability by Qβ replicase. For example, with reference to Table 1 of Example 3 and the Sequence Listing, SEQ ID NO: 9 differs from nv(+)DNA SEQ ID NO: 1 by insertion of a 5'-GGAT between bases 15 and 16, insertion of a T between bases 45 and 46, change of base 48 from C to A, and insertion of a 24-base segment between bases 49 and 50. Similarly, again with reference to Table 1 of Example 3 and the Sequence Listing, SEQ ID NO: 10 differs from nv(+)DNA SEQ ID NO: 1 by the insertion of a 48-base segment between bases 37 and 38. Similarly, mdvDNA could be easily modified by, for example, insertion of DNA at the XhoI site to provide additional DNAs that are amplifiable in accordance with the invention.

Targets

Any sample containing a nucleic acid, in purified or nonpurified form, can be used to provide nucleic acid target, for the target-dependent processes of the invention, provided the sample is at least suspected of containing the target. Examples include both DNA or RNA targets, including messenger RNAs, single-stranded or double-stranded RNAs or DNAs, or DNA-RNA hybrids. Further, the target nucleic acid segment may be a small segment of a much larger molecule although it will typically be at least about 10 and more typically 20–50 nucleotides long. Further still, the target nucleic acid may have a plurality of target nucleic acid segments, which may be the same or different.

Oligonucleotides

The present invention incorporates methods for the synthetic preparation of DNA, RNA or chimeric oligonucleotides. In this regard, reference is made to Applied Biosystems Model 380B DNA Synthesizer Users Manual, Version 1.11, November, 1985; Beaucage, et al. (1981), Tetrahedron Letts. 22:1859–1862; Mateucci and Carruthers (1981), J. Am. Chem. Soc. 103:3185–3191; Sinka, et al Tetrahedron Lets. 24:5843–4846.

The oligonucleotides may be prepared using any suitable method, such as, for example, the phosphotriester and phosphodiester methods, phosphoramidite methods, or automated embodiments of any of them.

The present invention is directed to the use of the DNA-dependent RNA polymerase activity of Qβ replicase and other RNA replicases to generate multiple reporter molecules. Each DNA or chimeric nucleic acid segment, which is a template for a replicase and is associated with a target segment can be used to generate greater than $10^9$ reporter molecules in this fashion.

The present invention is also directed to several applications relating to the discovery of the DDRP activity of RNA replicases. Examples of five different methods which have been devised to take advantage of this discovery include the following. These various methods illustrate how a complex segment or broken complex segment, which is amplifiable on account of the DDRP activity of an RNA replicase can be provided to.a sample as a pre-formed, single nucleic acid, which comprises a complex segment which has the sequence of an RNA that is autocatalytically replicatable by the replicase, or as one or more nucleic acids which can be processed or reacted in the sample to provide a nucleic acid which comprises a complex or broken complex nucleic acid segment which has the sequence of an RNA that is autocatalytically replicatable by the replicase.

Example 1 Hybridization/Separation/Amplification
Example 2 Nuclease Protection/Amplification
Example 3 Ligation/Amplification
Example 4 Double Extension/Amplification
Example 5 cDNA Synthesis/Amplification It will be explained in the following sections that several of these methods have more than one possible format depending on the number and characteristics of the probes being used.

In its most general sense, the invention is a method for amplification of a nucleic acid molecule comprising at least one 2'-deoxyribonucleotide and which amplification includes the use of the DDRP activity of an RNA replicase in one or more of its steps. The invention is also directed to methods for target nucleic acid segment-dependent amplification of reporter molecules dependent upon such DDRP activity in one or more of its steps. Further, detection of these reporter molecules indicates presence of the target nucleic acid in a sample containing nucleic acid. The reporter molecules may have uses other than to provide detectability of the presence of target nucleic acid segment (and target nucleic acid) in a sample. These other uses include use as probes, cloning intermediates, substrates for sequence analysis, and in other molecular biological or molecular genetic methods.

The invention also entails kits for carrying out the methods.

These methods and kits are particularly usefully applied in connection with nucleic acid probe hybridization assays for detection of target nucleic acid analytes. Thus, the invention also entails methods, and kits for carrying out the methods, for detecting the presence of a nucleic acid analyte in a sample.

Again, the various aspects of the invention entail applications in (and related kits for) amplifying target segments, detecting target nucleic acid analyte, and other procedures, of the discovery that Qβ replicase or another RNA replicase can use a complex DNA or chimeric nucleic acid, which has the sequence of an RNA that is autocatalytically replicatable by the replicase, as a template for catalyzing synthesis of the RNA of complementary sequence. Because this RNA is also autocatalytically replicatable by the replicase, the process of making the RNA from the DNA or hybrid nucleic acid initiates an autocatalytic replication of the RNA and its RNA complement catalyzed by the RNA-dependent RNA polymerase activity of the replicase. The substrate for the DDRP activity of a replicase in accordance with the invention must be a complex nucleic acid segment, as defined hereinabove, which has the sequence of a RNA that is autocatalytically replicatable by the replicase.

Following are summaries of various of the many embodiments of the present invention.

Embodiment 1

Hybridization/Separation/Amplification

In this format, the method of amplifying a nucleic acid segment in a sample includes mixing a probe with the sample containing the target nucleic acid under hybridizing conditions. The free (i.e. unhybridized) probes are separated from those which are hybridized with the nucleic acid in the sample. The system with hybridized probes is then subjected to amplification conditions and the amplified molecules are detected. A probe for this format may have the anti-target segment covalently linked at either its 3'- or 5'- terminus to the replicase-amplifiable segment or may have the anti-target segment embedded within the, and as part of, the replicase amplifiable segment. The reporter segment of the probe may be the entire replicase amplifiable segment or a reporter subsegment embedded within the replicase-amplifiable segment. The "reporter segment" has the sequence of the segment of amplified product that is assayed for in detecting whether amplification has occurred (i.e., whether target nucleic acid is in the sample being analyzed.) The probe may be a linear molecule. Alternatively, the probe may be a circular molecule wherein one terminus of the replicase-amplifiable segment is joined directly (i.e., through a single phosphodiester) to the anti-target segment and the other terminus is joined to the anti-target segment either directly or through a connector segment.

With reference now to FIG. 1, the present invention in one aspect, is a method for target nucleic acid segment-dependent amplification of a reporter molecule, which method comprises the following steps 1a–1d as illustrated:

1a) An anti-target segment (sequence) covalently linked at either its 3' or 5' terminus to an amplifiable sequence, e.g., nv(+)DNA, is mixed with a sample containing the target sequence under hybridizing conditions to cause the hybridization of the target and anti-target sequences.

1b) Column chromatography, or other means known to the art, is used to separate the hybrids which have formed from the unhybridized probe molecules.

1c) The amplifiable segments of the hybrid molecules are amplified via the DDRP activity of, e.g., Qβ replicase, to produce multiple RNA copies, e.g., nvRNA.

1d) The amplified material generated in 1c may be detected by suitable means known in the art.

Figure 2:
FIG. 2 is a schematic drawing illustrating alternate forms which a probe can take for use in the method described in FIG. 1.
Figure 2:
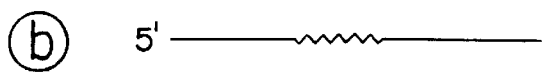
Figure 2:
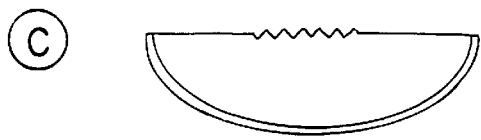
Figure 2:
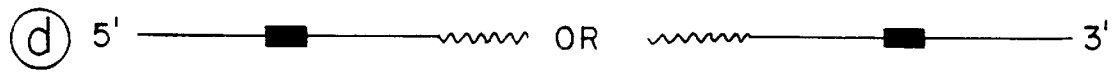

Reference is now made to FIG. 2, which schematically illustrates alternate probe constructs for use in the hybridization/separation/amplification format of FIG. 1. In the probes illustrated in the Figures, including FIG. 2, straight lines indicate entire, or partial, replicase-amplifiable segments (sequences); wavy lines in probe indicate anti-target segments (which may also be part of replicase amplifiable segment) and wavy lines in target indicate target segments; the double line indicates a connector sequence; and the solid box indicates a reporter segment. The terms "segment" and "sequence" are used interchangeably to mean a segment with a particular sequence.

In the process of FIG. 1, the probe molecule may have an amplifiable sequence joined directly (e.g., through a single phosphodiester) to anti-target sequence at either terminus (2a, 2d) or the anti-target segment may be internal to and part of the amplifiable segment (2b, 2c). A connector sequence may be used to circularize the probe (2c). A reporter segment may be present internal to the amplifiable segment (2d). Any of these probe constructs may be used in the hybridization/separation/ amplification format described above and illustrated in FIG. 1.

Embodiment 2

Nuclease Protection/Amplification

In this format, the probe comprises an anti-target segment adjacent the 3'-end or the 5'-end of the replicase amplifiable segment. The anti-target segment of the probe is selected, and the nucleic acid of a sample thought to comprise target nucleic acid is treated, so that probe hybridized to target is protected from digestion by a pre-selected nuclease. A sample of nucleic acid is hybridized with probe, the pre-selected nuclease is added to degrade probe that failed to hybridize, then amplification is effected by adding an RNA replicase which recognizes the replicase-amplifiable segment of the probe as a template for DDRP activity. The molecules made in the resulting amplification (if target was present) may be detected. Examples of enzymes providing suitable nuclease activities include *E. coli* endonuclease VII, T4 DNA polymerase, and Klenow Fragment of *E. coli* DNA polymerase I.

Figure 3:
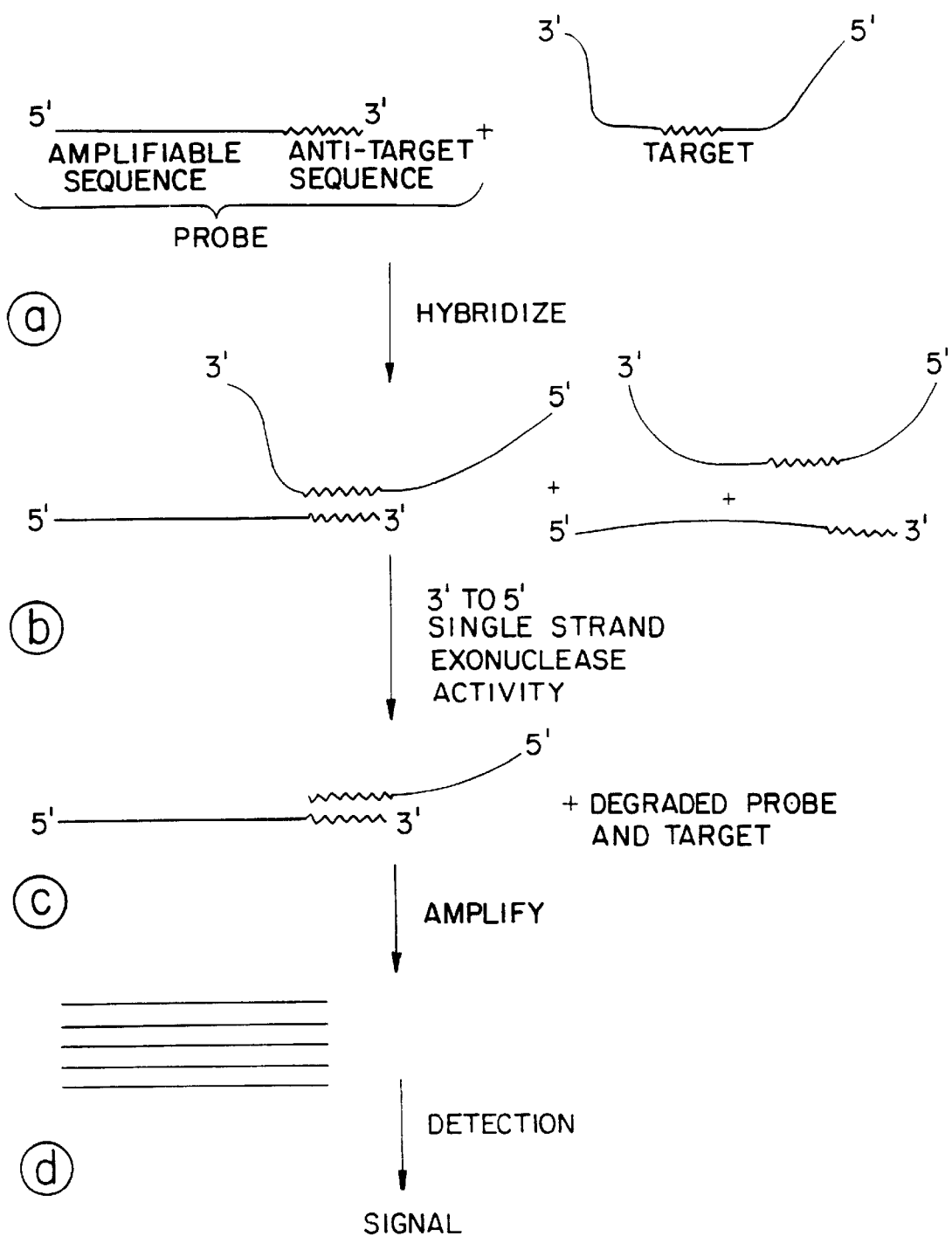
FIG. 3 is a schematic drawing illustrating another aspect of the present invention for a target nucleic acid segment-directed amplification of a reporter molecule. In the method illustrated in FIG. 3, probe is hybridized to target and then an enzyme with single-stranded 3'-to-5' single-stranded exonuclease activity is added to degrade any probe which is not protected from degradation by being hybridized to target. Finally, protected, undegraded probe is amplified. As illustrated in the Figure, the amplified product may be detected.

Referring now to FIG. 3, there is schematically illustrated a method for a target nucleic acid segment-dependent amplification of a reporter molecule, comprising the following steps 3a–3d:

3a) In the nuclease protection/amplification format, a target nucleic acid sequence and a probe, comprising, attached directly at its 3'-terminus, an amplifiable portion of nv(−)DNA, nv(+)DNA or other amplifiable DNA is subjected to conditions which allow hybridization of the target and anti-target sequences to occur.

3b) The product of step 3a is subjected to nuclease digestion from the 3'-terminus of unhybridized probe using the 3'- to 5'-single-stranded nuclease activity of Klenow Fragment of *E. coli* DNA polymerase I, T4 DNA polymerase, or other suitable enzyme. The remaining probe molecules, protected from nuclease digestion because of their association with target via hybridization, can be amplified with a replicase to synthesize amplification products (i.e., reporter molecules).

3c) The strands of probe which survived the nuclease digestion step in accordance with Step 3b are amplified using Qβ replicase, or another replicase, and relying on the DDRP activity of such enzyme using as template the amplifiable segment of the probe.

3d) The molecules generated in accordance with the amplification of Step 3c may be detected by suitable means known to those skilled in the art.

Embodiment 3

Ligation/Amplification

In this format, the sample is treated under hybridizing conditions with a first non-amplifiable probe and a second non-amplifiable probe, each probe comprising part of an amplifiable nucleic acid segment, said part joined directly to anti-target nucleic acid sequences. In one probe, the anti-target sequence is joined at its 5'end to a 5'-part of an amplifiable segment. In the other probe, the anti-target sequence is joined at its 3'-end to the 3'-remainder of the amplifiable segment. The anti-target sequences are selected so that, when hybridized to target, they will be adjacent one another and are capable of being ligated. After hybridization, the first and second probes are joined by treatment with a ligase enzyme, such as T4 DNA ligase or *E. coli* DNA ligase, to produce a replicase-amplifiable molecule. Upon amplification, the amplified molecules may then be detected.

Figure 4:
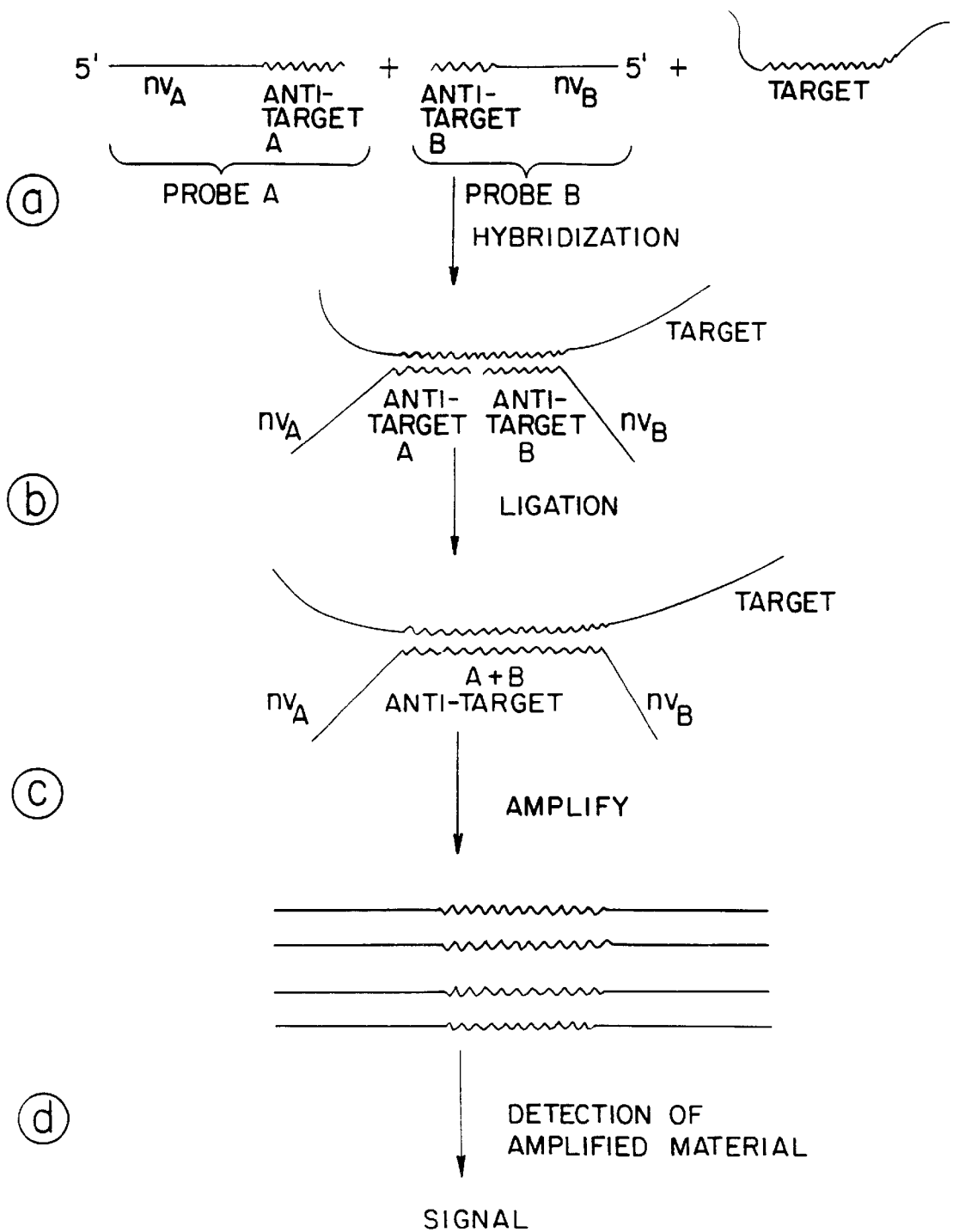
FIG. 4 is a schematic drawing illustrating another aspect of the present invention for a target nucleic acid segment-directed amplification of a reporter molecule. In the method illustrated in FIG. 4, two probes are hybridized to adjacent segments of target and ligated and then the resulting ligated probe is amplified. As illustrated in the Figure, the amplified product may be detected.

Referring now to FIG. 4, there is schematically illustrated a method, involving the Ligation/Amplification format, for a target nucleic acid segment-dependent amplification of a reporter molecule, comprising the following steps 4a–4d.

4a) Two non-amplifiable probes, A and B, each contain a part of an amplifiable sequence (both parts together being the amplifiable sequence), e.g., $nv_A$ and $nv_B$, respectively, linked directly to portions of an anti-target sequence, e.g., anti-target A and anti-target B respectively. The two probes are mixed with a nucleic acid comprising target under hybridizing conditions.

4b) The probes are ligated via the anti-target sequences using T4 DNA ligase, *E. coli* DNA ligase or other enzyme to provide suitable ligase activity to produce a molecule which is amplifiable.

4c) The ligated probes are amplified using a replicase (e.g. Qβ) and relying on its DDRP activity.

4d) The amplified material generated in accordance with Step 4c may be detected by suitable means known to those skilled in the art.

Several modifications of this format may be employed. First, it is possible to use as probe a single molecule, wherein the 5'-terminus of the 5'probe (probe A in FIG. 4) is joined directly (e.g., by a phosphodiester bond or other short covalent linkage that does not entail a nucleoside) to the 3'-terminus of the 3'-probe (probe B in FIG. 4). Alternatively, the probe may be circular, i.e., the termini may be joined by a connector sequence, or a circle may be formed by the ligation after hybridization. The ligation would then result in a single-stranded circle with an amplifiable segment.

A second modification is to eliminate the ligation step and employ the broken complex segment as the template for the DDRP activity. Although the efficiency of amplification is reduced by this alteration, a step in the procedure is saved.

A third modification of this method is to design the two probes such that anti-target A and anti-target B hybridize to sequences which are not precisely adjacent to one another. In this case, an additional DNA polymerization step which follows hybridization and precedes ligation, will fill in the intervening sequence to form a broken complex segment, which may be used as a template for the DDRP activity without ligation or may be ligated and then used as a template for the DDRP activity. This altered format offers the advantage of amplification of the segments (the sequences of which might not be known) between the target segments in addition to the amplification of target (and anti-target) segments.

Finally, one or both probes may be amplifiable by themselves. In such cases, the amplified products of ligated molecules will differ from those of the probes alone. This difference may be detected using general methods of analysis known to those skilled in the art.

Embodiment 4

Double Extension/Amplification

In this format, a probe consisting of a portion (including the 5'-terminus) of a replicase-amplifiable sequence covalently joined at its 3'-terminus with an anti-target sequence is mixed under hybridizing conditions with a sample containing a nucleic acid. The hybrids resulting if target is present are treated with an enzyme providing DNA polymerase or reverse transcriptase activity to extend the hybridized probe from the 3'-terminus in a primer-dependent extension reaction using target as template. The product of the extension is separated from the target, as by thermal denaturation, and hybridized with a second probe consisting of a portion (including the 5'-terminus) of replicase-amplifiable sequence covalently joined at its 3' terminus with sequence that is the same as that of a sequence of target that is located 5' from the target sequence of the first probe. The portion of the amplifiable sequence of the second probe is from an amplifiable sequence that is the complement of the amplifiable sequence, of which a portion is at the 5'-terminus of the first probe. The sequence of target in the second probe is complementary to a sequence in the part of extended first probe added in the extension. Thus, hybridization of the second probe will occur with the extended product of the first probe, but not with the first probe itself. The denatured extended first probe is hybridized with the second probe. The resulting hybrid is used as a template for a primer extension by an enzyme providing DNA polymerase activity. The product of this extension is amplified with a replicase, and the amplified molecules are detected.

Examples of enzymes providing the DNA polymerase activity that may be used in the primer extensions, of this or any other embodiment of the invention, are *E. coli* DNA polymerase I, Klenow Fragment of *E. coli* DNA polymerase I, avian myeloblastosis virus reverse transcriptase, Moloney murine leukemia virus reverse transcriptase, *Thermus aquaticus* DNA polymerase, *M. luteus* DNA polymerase, T4 DNA polymerase, T7 DNA polymerase, *Thermus thermophilus* DNA polymerase, *Thermus flavus* DNA polymerase, *Bacillus licheniformis* DNA polymerase, *Bacillus stearothermophilus* DNA polymerase, or other DNA polymerases, reverse transcriptases, or enzymes with a primer-initiated, template-dependent DNA polymerase activity. Examples of enzymes providing the reverse transcriptase activity that may be used in the primer extensions, of this or any other embodiment of the invention, are avian myeloblastosis virus reverse transcriptase, Moloney murine leukemia virus reverse transcriptase, the reverse transcriptase of any other retrovirus or of a retrotransposon, *Thermus aquaticus* DNA polymerase, or other enzymes with reverse transcriptase activity.

The two probes may be added at different times or simultaneously, although if the strand-separation of the first extension product from target employs thermal denaturation at a temperature that denatures the polymerase employed in the first extension, additional polymerase will need to be added for the second extension.

Figure 5:
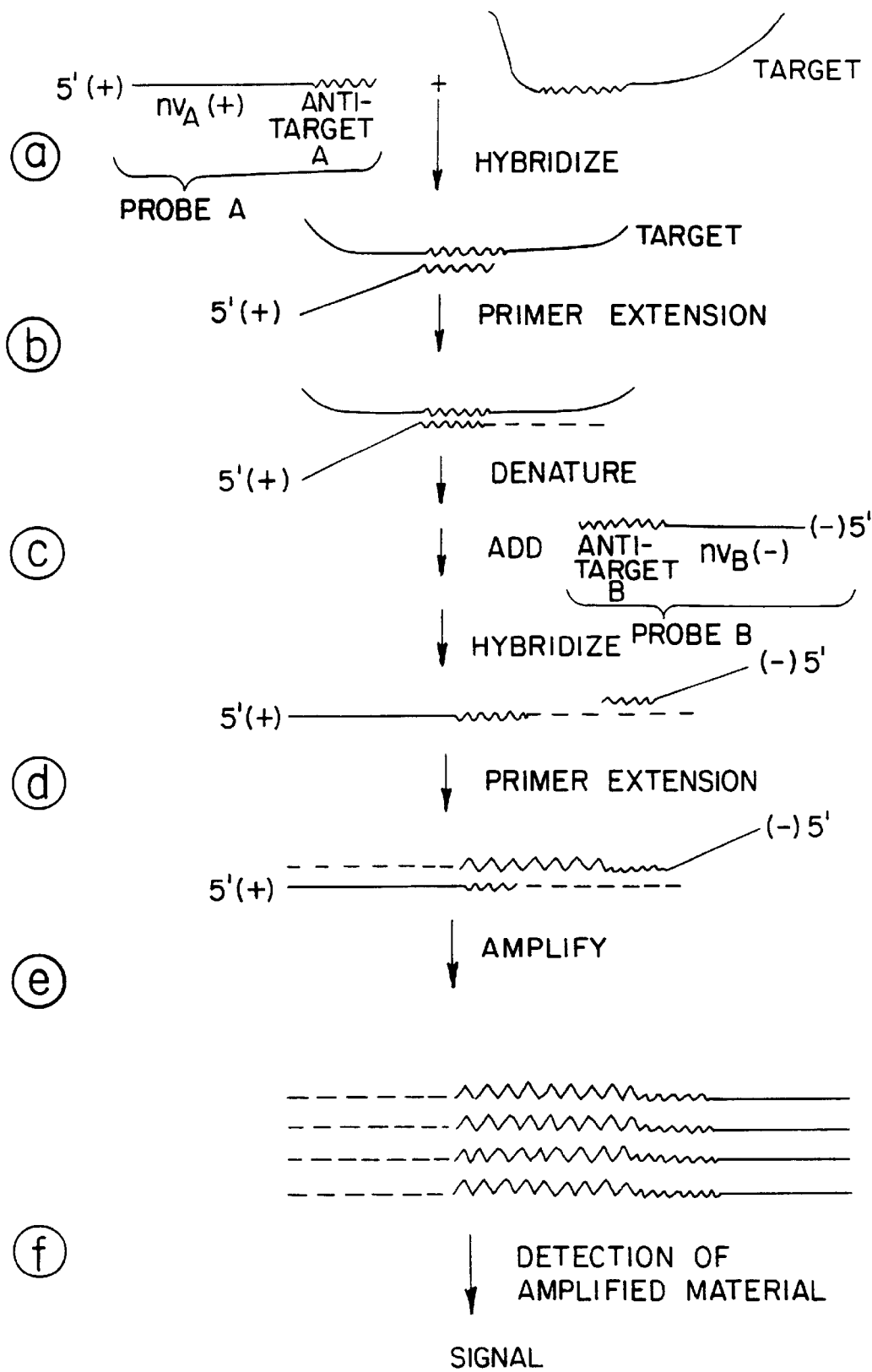
FIG. 5 is a schematic drawing illustrating another aspect of the present invention for a target nucleic acid segment-directed amplification of a reporter molecule. In the method illustrated in FIG. 5, a first probe is hybridized to target and primes chain extension with target as template, the product of the chain extension is strand-separated, a second probe is hybridized to the extended first probe and primes chain extension with extended first probe as template. The product of this second chain extension comprises a replicase amplifiable segment which, in turn, comprises a segment which has the sequence of a segment of the target. Amplification is carried out with the product of the second chain extension. As illustrated in the Figure, the amplified product may be detected.

Referring now to FIG. 5, this embodiment relates to a method for a target nucleic acid segment-dependent amplification of a reporter molecule using a Double Extension/Amplification format and comprises the following steps 5a–5f:

5a) Two probes A and B, as described for the Double Extension/Amplification Format, are employed. These probes are not complementary to one another, i.e., prior to the extension of Probe A, the two probes are not capable of hybridizing to one another under hybridizing conditions employed in the procedure with sufficient stability to prime a template-dependent, primer-initiated DNA extension reaction). Probe A may comprise at its 5'-end a non-amplifiable, 5-'-portion of nv(+)DNA. Probe B would then comprise at its 5'-end a non-amplifiable 5'-part of nv(−)DNA (i.e., the nanovariant DNA strand with the sequence complementary to that of the nanovariant DNA strand of which the 5'-end of Probe A is a part). The anti-target sequences of the two probes will provide specificity and be effective to prime primer-dependent DNA synthesis on templates; thus, they will be at least about 10 and more typically 20–50 nucleotides in length. In step 5a, the mixture of Probe A and nucleic acid is subjected to conditions which cause the hybridization of target with anti-target sequences in the Probe.

5b) The hybrid which occurs if target is present is treated with a DNA polymerase or reverse transcriptase to generate adjacent anti-target nucleic acid sequences by primer extension from the 3'-terminus of Probe A as primer hybridized in accordance with Step 5a.

5c) The extended probe strands produced in accordance with Step 5b are separated from the original target by thermal denaturation. The original probe A, now having an extended sequence as created in accordance with Step 5b, is then hybridized with probe B. Depending on the segment of target nucleic acid selected to provide the sequence of the 3'-anti-extended-Probe A segment of Probe B, Probe B may hybridize immediately adjacent to the anti-target segment originally present in probe A, or to a segment of extended Probe A that is 3from the 3'-end of this "original" anti-target segment. Typically the segment to which probe B hybridizes will be within 2000 nucleotides of the 3'-end of the original anti-target segment and usually much closer. It is noteworthy that carrying out this method does not require knowledge of the sequence of the segment of target between the 3'-end of the target segment of probe A and the 5'-end of the target segment also present at the 5'-end of probe B.

5d) An amplifiable DNA is then generated by primer extension from Probe B as primer hybridized to extended Probe A in accordance with step 5c.

5e) The amplifiable molecule(s) generated in Step 5d is amplified via a replicase, employing its DDRP activity.

5f) The amplified material may be detected by suitable means known to those skilled in the art.

The process may be modified by using, as Probe A or Probe B or both, probe(s) that is (are) amplifiable. In this case, the amplified material produced in Step 5e can be distinguished from that of the original probes A (and B) by suitable means known to those skilled in the art. Additionally, the process may be modified to include other uses of amplified material in addition to providing detectability for the presence of target in a sample.

Embodiment 5 cDNA Synthesis/Amplification

In this format, an RNA probe consisting of a replicase-amplifiable sequence covalently joined at its 3'-terminus with an anti-target sequence is mixed with the nucleic acids in the sample under hybridizing condition. The hybridized molecules are then treated with a reverse transcriptase enzyme. The RNA portion of the resulting RNA-DNA hybrid, and unhybridized RNA probe, are then destroyed. All or part of the remaining DNA sequence is then amplified using a replicase enzyme, that can be employed to amplify the replicase amplifiable segment of the RNA probe, and the resulting amplified molecules may then be detected. Examples of the reverse transcriptase enzyme include avian myeloblastosis virus reverse transcriptase, Moloney murine leukemia virus reverse transcriptase, and Thermus aquaticus DNA polymerase. The destruction of unhybridized probe and the RNA portion of the RNA-DNA hybrid is enhanced under basic conditions, such as by the addition of sodium hydroxide. The destruction of the RNA portion of the RNA-DNA hybrid may also be accomplished enzymatically with suitable enzymes, such as RNase H from *E. coli* or other species. Free probe can be digested using various ribonucleases.

Figure 6:
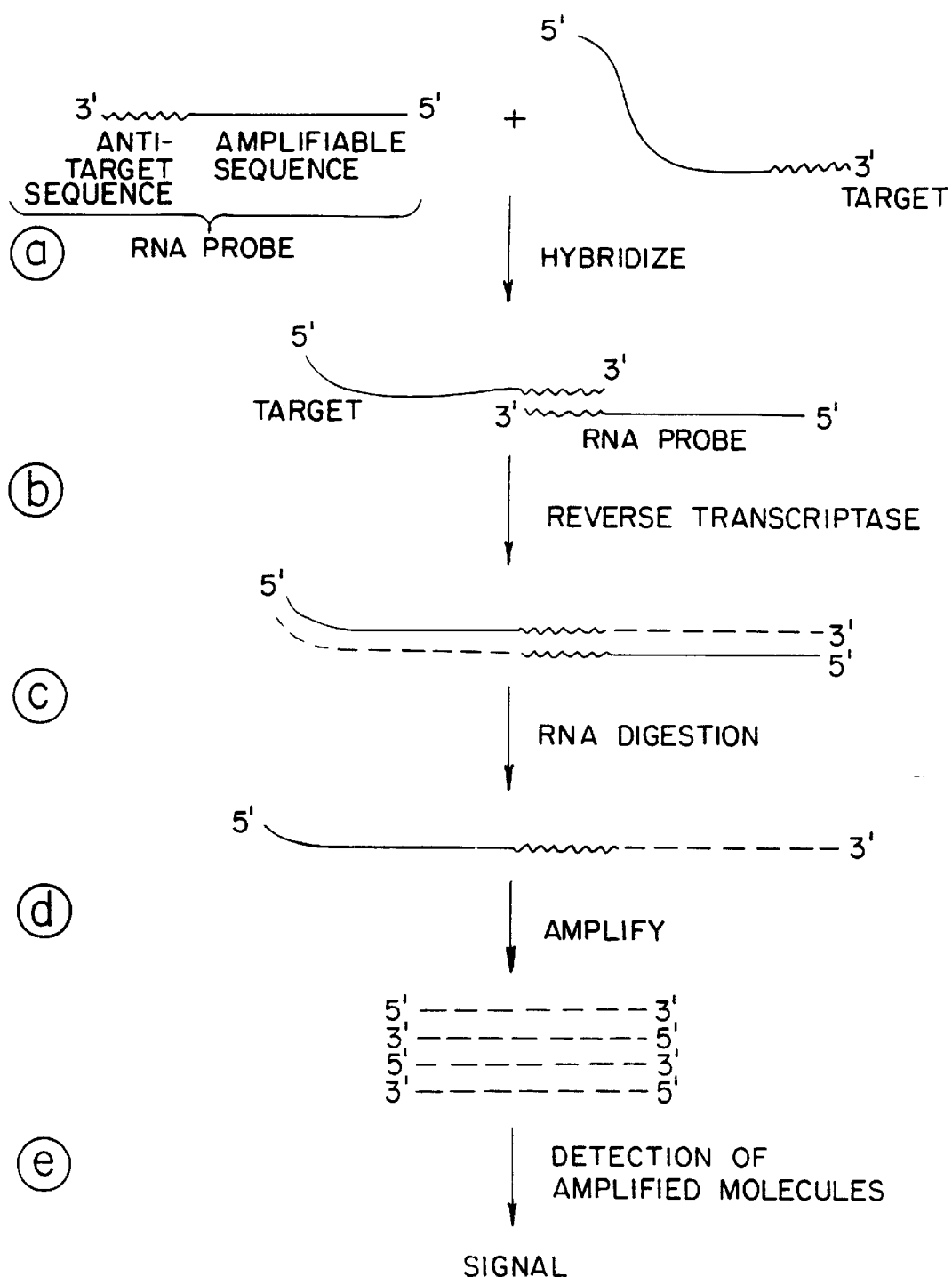
FIG. 6 is a schematic drawing illustrating another aspect of the present invention for a target nucleic acid segment-directed amplification of a reporter molecule. In the method illustrated in FIG. 6, an RNA probe is used and the target segment is at the 3'-end of target nucleic acid. After hybridization of probe to target, both are extended in chain extension reactions, then RNA is digested and amplification is carried out with replicase-amplifiable DNA added to target in the chain extension of target. As illustrated in the Figure, the amplified product may be detected.

Referring now to FIG. 6, this embodiment is a method for a target nucleic acid segment-dependent amplification of a reporter molecule, employing the CDNA Synthesis/Amplification Format and comprising the following steps 6a–6e.

6a) A target nucleic acid sequence is hybridized with an amplifiable RNA probe comprising a portion of nv(+) RNA, nv(−)RNA or other amplifiable RNA attached covalently to anti-target nucleic acid sequence(s) at its 3' terminus. The 3'-end of the target segment is at the 3'-end of target molecule and, in the hybrid with RNA probe, is complementary to the nucleotide at the 5'-end of the anti-target segment.

6b) The strands of the hybrid molecule are elongated by primer extension in the presence of AMV Reverse Transcriptase or another suitable reverse transcriptase.

6c) Unhybridized RNA probe and chain-extended RNA is digested either chemically, e.g., and sodium hydroxide treatment or enzymatically, e.g., RNase treatment. Unhybridized probe may be removed prior to step 6b.

6d) The treated sample is neutralized with an acid or buffer (in the case of sodium hydroxide treatment described in Step c) or RNase inhibitor (in the case of RNase treatment).

6e) The DNAs generated in Step c have amplifiable segments, and these are amplified via the DDRP activity of a replicase which is capable of autocatalytically replicating the amplifiable segment of the RNA probe.

The amplified material may be detected by suitable means known to those skilled in the art.

Several specific additions and modifications to this format may be useful for specific applications. For example, the method requires that a 3' terminus terminal hydroxyl be available at the end of the target sequence for the elongation process described in Step 6b. If the target does not present itself in this fashion, digestion of the target sequence at a defined site with a restriction endonuclease prior to denaturation and hybridization is one option. A second option is to generate random target 3'-ends by shearing, chemical cleavage, or digestion with nucleases prior to hybridization. A third option is to treat the hybrids formed in Step 6a in the presence of both an enzyme to provide 3'- to 5'-exonuclease activity and an enzyme to provide reverse transcriptase activity. The exonuclease activity will trim back the overhanging 3'-terminus of the hybridized sample nucleic acid to the portion which complements the anti-target portion of the probe. The reverse transcriptase activity will then extend the sequence from the hybridized 3'-hydroxyl terminus.

Figure 7:
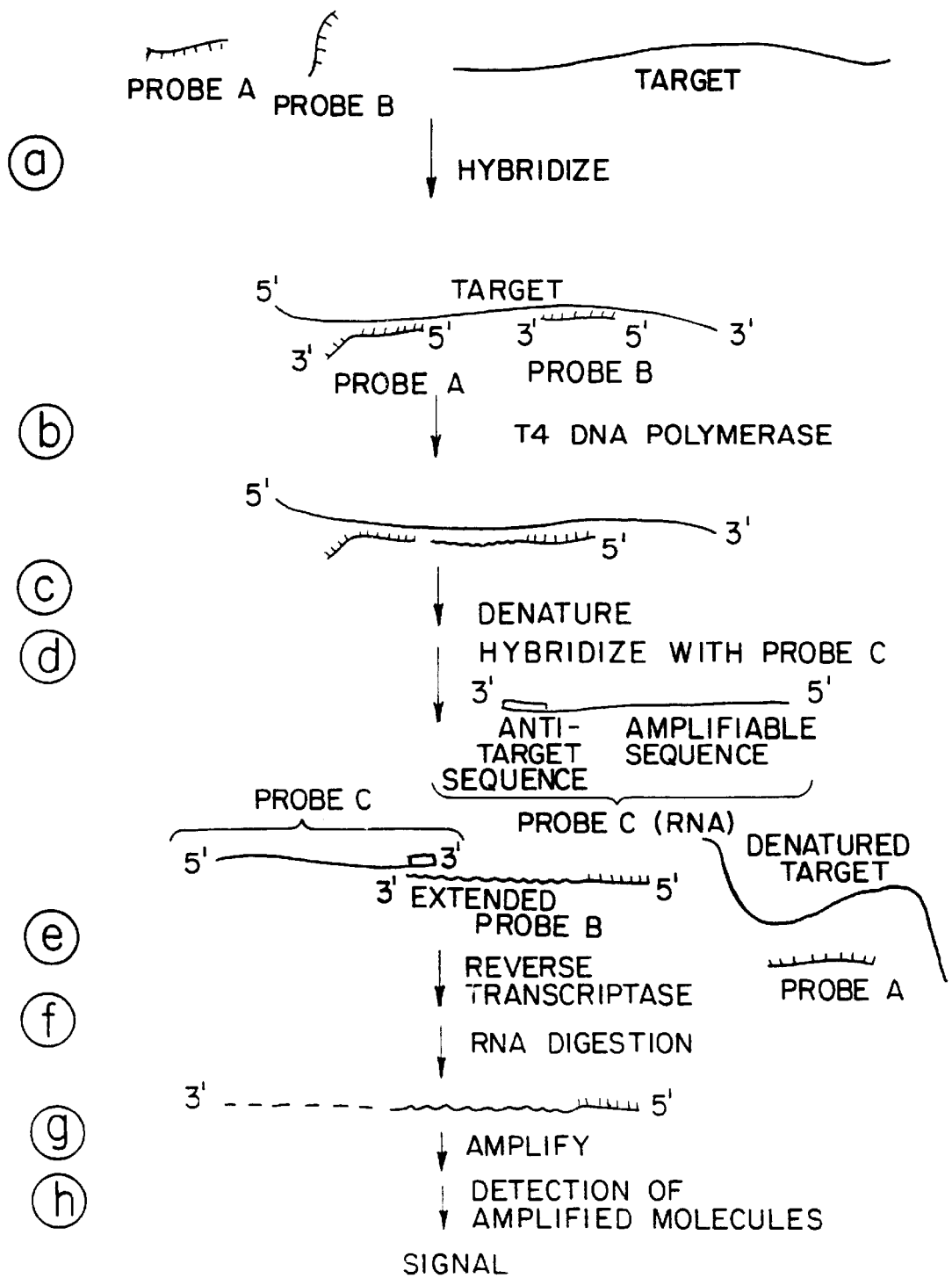
FIG. 7 is a schematic drawing illustrating another aspect of the present invention for a target nucleic acid segment-directed amplification of a reporter molecule. In the method as illustrated in FIG. 7, three probes, designated A, B and C, are employed. Probes A and B lack replicase-amplifiable segments. Probe C is an RNA and comprises a replicase amplifiable segment. Probes A and B hybridize to target segments separated by a gap, the target segment for A being located 5' from that for B. The anti-target segment of C, which is actually a "target-like segment," has the same sequence as the segment of target adjacent to and immediately 3' from the 3'-end of the target segment for A. Probes A and B are hybridized to target and at least B is chain extended to the 5'-end of A. The product of the chain extension is strand-separated and probe C is hybridized to chain-extended B and another chain extension is carried out, RNA is digested, and amplification is carried out beginning with the replicase amplifiable segment added in the second chain extension of B. As illustrated in the Figure, amplified product may be detected.

Referring now to FIG. 7, a fourth method for generation of the required 3'-terminal hydroxyl at the end of the target sequence comprises the following steps 7a–7d:

7a) A target nucleic acid is hybridized with two probes, A and B, such that, when hybridized, the probes are separated by an intervening gap of at least one, and more typically at least several, up to about 2000, nucleotides. Probe A may be DNA, RNA or a chimeric nucleic acid. Probe B is preferably DNA as it and its extension products must be resistant to degradation under conditions which degrade RNA.

7b) Probe B, which is hybridized to a target segment located 3' from the segment to which Probe A hybridizes, is elongated by primer extension in the presence of T7 DNA polymerase, T4 DNA polymerase, *E. coli* DNA polymerase I, or Klenow Fragment thereof, or another suitable polymerase or reverse transcriptase to catalyze the extension reaction.

7c) The extended probe B is separated from the target nucleic acid by means familiar to those skilled in the art, e.g. thermal denaturation. Note that the extension of Probe B is blocked by Probe A to provide a defined, 3'-end to Probe B.

7d)–7h) The separated, extended probe B is then used, with a third probe, probe C, which is an RNA with the same functional properties, relative to extended probe B, as the RNA probe of FIG. 6 to generate reporter molecules which may be detected. Steps 7d)–h) correspond to steps 6a)–6e), respectively.

Another modification of the cDNA Synthesis/Amplification format is to replace the RNA probe with a chimeric molecule comprising deoxyribonucleotides and at least two ribonucleotides, such that the replicase-catalyzed autocatalytic replicability of the chimeric molecule can be destroyed with alkaline or RNase treatment. PM1500, which has two pairs of ribonucleotides, is an example of an RNA that could be used as the amplifiable segment of such a chimeric probe, albeit the process using a probe with such an amplifiable segment proceeds with substantially reduced efficiency in comparison with the completely RNA probe of the same sequence, as complete digestion of the chimeric probe which is required to reduce "background" to a minimum is more difficult than with the completely RNA probe. All the steps of the method with a chimeric in place of a completely RNA probe can be performed as described in this section.

Detection Methods

The detection of amplified products can be performed by methods and materials familiar to those skilled in the art. Such detection methods include reactions of RNA with dyes and detection of the dye-RNA complexes. Especially in situations where the RNA amplification product is present in a significant background of other nucleic acids, which would also form complexes with a dye, detection of amplification product by formation of dye-RNA complexes can be accompanied by separation (as by electrophoresis, chromatography or the like) according to size of nucleic acid of a sample thereof in which an amplification reaction has been carried out in order to detect the product(s) of the amplification reaction, which will have characteristic size(s). Confirmation that nucleic acid of the expected size found in a sample using dye-staining after an amplification reaction according to the invention is RNA from the amplification reaction can be obtained by using a sequence-specific detection method, such as a nucleic acid probe hybridization method, as described below. The dyes include chromogenic dyes such as "stains all" (Dahlberg, et al. (1969), J. Mol. Biol., Vol 41, pp. 139–147), methylene blue (Dingman and Peacock (1968), Biochemistry, Vol. 7, pp. 659–668) and silver stain (Sammons, et al. (1981), Electrophoresis, Vol. 2, pp. 135–141; Igloi (1983), Anal. Biochem., Vol. 134, pp. 184–188) and fluorogenic compounds that bind to RNA, including ethidium bromide (Sharp, et al. (1973), Biochemistry, Vol. 12, pp. 3055–3063; Bailey and Davidson (1976), Anal. Biochem., Vol. 70, pp. 75–85), acridine orange, propidium iodide and ethidium heterodimer.

Additional means of detection which are familiar to those skilled in the art include the use of modified ribonucleoside triphosphates during the amplification reaction, leading to incorporation of modified, detectable ribonucleotides specifically into the amplified products, followed by separation (e.g., chromatographically, electrophoretically) of amplification products from unincorporated, modified ribonucleoside triphosphates, prior to detection of the amplified products based on signal directly from the label of the modified, incorporated ribonucleotides or produced by subsequent reactions of the amplified products dependent on the presence of such label. Most commonly, a modified ribonucleotide is radioactively labeled with an isotope such as $^{32}$P or $^{35}$S. The detection of beta particle emissions from such isotopes incorporated into RNA resulting from amplification according to the invention is performed by methods, such as scintillation counting or autoradiography, well known in the art. Ribonucleoside triphosphates, which are modified to carry a luminescent, fluorescent or chromogenic moiety on the base, can also be incorporated into the amplification product and then detected by various methods and means familiar to those skilled in the art. Other modifications of ribonucleoside triphosphates that can be tolerated by the replicases for incorporation of the modified ribonucleotides into amplification products include those where the bases are linked to "affinity molecules" such as biotin, antigens, enzyme inhibitors, or the like, which provide detectability to the amplification products through subsequent reaction with, e.g., enzyme-labeled avidin or streptavidin reactive with biotin, enzyme-labeled antibody specific for an antigen affinity molecule, or complex of enzymes reactive with an enzyme-inhibitor affinity molecule, as understood by the skilled. For example, reaction of biotin linked to an uracil moiety in amplification product with avidin or streptavidin conjugated to a detectable material as described previously or to an enzyme to catalyze a reaction with substrates which react to produce detectable (e.g., colored) materials, is a familiar means of detection to those skilled in the art.

Additional means of detection of products of amplification in accordance with the invention which are familiar to those skilled in the art include hybridization of a sample of nucleic acid thought to include such product with a nucleic acid probe which comprises a segment with the entire sequence of the product or a pre-selected portion of such sequence (a "reporter" sequence or segment). Note that the amplification product, because it results from a process including autocatalytic replication, will include RNA with the sequence of the DNA segment that was the substrate for the DDRP activity of the replicase and RNA with the complementary sequence. Probes to both such RNAs may be employed simultaneously, particularly in situations where one of the two might be present in a significant excess over the other. The nucleic acid probe will be labelled in some way to make it detectable, e.g., will include at least one radioactively labelled or otherwise modified nucleotide as described above in connection with labelling of the amplification product per se or may be labelled directly (covalently and prior to use in hybridization with target of the probe), with an enzyme which can catalyze a signal-producing (e.g., chromogenic) reaction. Methods and means for detecting amplification product via nucleic acid probe hybridization are also well known to the art. For example, if nucleotides which carry biotin are incorporated into the nucleic acid as described in Forster (1985), Nucleic Acids Res. and Lange (1981), Proc. Natl. Acad. Sci., USA, the products may be detected by first reacting them with a conjugate of avidin or streptavidin with a signalling moiety and then by detection of the signalling moiety. The signalling moieties could include luminescent, fluorescent or colored (chromogenic) compounds, enzymes which convert reactants to one of such compounds, or analytes which react in the presence of other reactants and/or an enzyme to produce a luminescent, fluorescent, or colored compound.

When the amount of the reporter RNA produced in an amplification reaction according to the invention is substantial, as the skilled understand, both in absolute amount (so that when complexed with a dye the RNA would be detectable even if no other nucleic acid were present) and compared with the amount of the nucleic acid of the original sample (so that "background" due to complexes between the dye and other nucleic acid will not make the complex of the dye with reporter RNA undetectable), the incorporation of radioactively or otherwise modified ribonucleotides or analysis by nucleic acid probe hybridization assay methods is not required for detection of amplified product. The amplified material can be detected directly by reaction with luminescent, fluorescent or colored dyes, often after separation according to size from other nucleic acids by, e.g., gel electrophoresis. The person of ordinary skill is capable of determining readily, for a given dye, given size of RNA product from amplification, and given process used for separation of nucleic acid by size, what the minimum detectable amount of amplification product would be if no other nucleic acid were present. Generally, amplification in accordance with the invention to provide RNA, made by autocatalytic replication, in at least a 100-fold molar excess relative to the DNA or chimeric template for DDRP activity with which the amplification is initiated will be adequate to distinguish such RNA, complexed with dye, from other, similarly sized nucleic acids in a sample, provided that the 100-fold molar excess of RNA is above the minimum detectable amount in the system that is used. As the skilled will understand, in many situations amplification to much lower levels (e.g., to provide only a 5-fold molar excess) will be adequate to provide detectability above background. In any case, amplifications to provide far in excess of the above-noted 100-fold molar excess will typically be carried out.

Alternative detection methods include detection of accumulation or depletion of one of the reagents involved in the amplification process. For example, during autocatalytic replication, the ribonucleoside triphosphate ATP is consumed as AMP is incorporated into the reporter RNA molecules. The concentration of ATP can be measured accurately using known methods which rely on bioluminescence catalyzed with a luciferase, such as a beetle luciferase (e.g., from *P. pyralis*). Thus, amplification in accordance with the invention could be detected by using bioluminescence catalyzed by a luciferase to detect depletion of ATP from a solution in which such amplification was occurring.

General Separation Methods After Amplification

The separation of RNA produced in amplification by autocatalytic replication and containing either normal or modified nucleotides or bound with dyes is generally conducted by methods and means known to the art. For example, amplified materials can be bound to filters or particles and unbound modified nucleotides or dyes can be separated and removed by suitable washing conditions. The binding process can be non-specific, e.g., binding all nucleic acids, but not unincorporated materials; or specific, binding only nucleic acids comprising particular sequences. or other properties. Specific binding can be directed by substances that are bound to any of various support materials (e.g., surfaces of wells on microtiter plates, latex or agarose beads (including magnetic beads), chromatographic resins, as understood in the art) and that are capable of complexing specifically with certain nucleic acids. For example, when the nucleic acid to be specifically bound is RNA amplification product resulting from amplification in accordance with the invention, such specific-binding substances include antibodies to specific classes of nucleic acids, e.g., double-stranded RNA, nucleic acids comprising a segment with a specific sequence complementary to a sequence in amplified product; or avidin or streptavidin to complex with biotin in the RNA produced in the amplification process as described previously.

Applications of the Invention Other than Production of Reporter Molecules

The products resulting from the DDRP activity of Qβ replicase and other RNA replicases may be used as nucleic acid probes in essentially any application in which RNA probes can be used. For example, a nanovariant RNA in which a probe sequence is incorporated can be made starting with a nanovariant DNA segment of the same sequence (or complementary) of the nanovariant, probe-sequence-containing RNA using the DDRP activity of a replicase and can be used in several hybridization formats which involve solid supports, including Southern hybridization, Northern hybridization, slot blot and dot blot hybridization, and in situ hybridization. Hybridization on other solid surfaces, such as latex beads or paramagnetic particles, and in solution may also be effective uses of the molecules from amplification. The RNA probe may, as indicated above, be labelled in the process of being made from the DNA or, being autocatalytically replicatable, can be used unlabelled to hybridize with target that may be present in a sample of nucleic acids being probed and then, if such hybridization has occurred, can be subjected to conditions for further autocatalytic replication (possibly with simultaneous labelling as described above) prior to detection.

The products from amplification in accordance with the invention could also be used in gene expression work. Introduction into an amplifiable DNA sequence of a cassette containing a translation initiation site upstream of a sequence coding for a peptide or protein, and use of the RNA, made by autocatalytic replication begun with the DDRP activity of a replicase using this construct as a template, in combination with a translation system, such as an X. laevis oocyte system or an in vitro rabbit reticulocyte lysate system, could yield significant amounts of a protein of interest.

The products from amplification could also be used as substrates for sequence analysis using standard methods for sequencing of RNA familiar to those skilled in the art.

In accordance with the present invention, complex amplifiable DNAs or chimeric nucleic acids could also be used in place of autocatalytically replicatable RNAs to label "affinity molecules," including antibodies, nucleic acid probes, and the like, as described, e.g., in Chu et al., PCT Application Publication No. WO87/06270 or U.S. Pat. No. 4,957,858, used in detecting analytes to which the affinity molecules bind specifically. The amplifiable, complex DNA or chimeric nucleic acid label could be treated, substantially as described in PCT Application Publication No. WO87/06270 or U.S. Pat. No. 4,957,858 for autocatalytically replicatable RNA label, to provide detectability to an affinity molecule. The RNA affinity molecules described in PCT Application Publication No. WO87/06270 and U.S. Pat. No. 4,957,858, which are autocatalytically replicatable by Qβ replicase or another RNA replicase and which also comprise an anti-target segment corresponding to a nucleic acid analyte can, in accordance with the present invention, be replaced with DNAs or chimeric nucleic acids of the same sequence or, as described above, readily made from such DNAs or chimeric nucleic acids. U.S. Pat. No. 4,957,858 is incorporated herein by reference.

Kits

In other embodiments, the invention relates to kits for carrying out the target nucleic acid segment-dependent amplification of reporter molecules according to the methods described above and to diagnostic kits for the detection of specific target nucleic acid analytes in a sample containing one or more nucleic acids in which at least one of the nucleic acids is suspected of containing a pre-selected target sequence. The kits are preferably packaged in multicontainer units having individual containers for each component. Examples of kits relating to this invention are as follows:

EXAMPLE 1 (Kit 1)

Hybridization/Separation/Amplification Kit

The Hybridization/Separation/Amplification Kit comprises at least two containers, packaged together, with the following components in separate containers:

(a) a hybridization solution comprising an oligonucleotide probe having a complex, amplifiable nucleic acid segment or a portion thereof and an anti-target nucleic acid segment (see the description below of kit 3 for the case that the probe has only a portion of an amplifiable segment, in such a case there must be at least two probes); and (b) an amplification buffer with Qβ replicase or another RNA replicase, which has DDRP activity with the amplifiable segment of the probe of component (a), said buffer suitable for the DDRP activity of said replicase.

A preferred hybridization solution comprises the following: 5×SSC (750 mM NaCl, 75 mM sodium citrate), 2% dextran sulfate, 40 mM sodium phosphate, pH 6.5, 0.1 mg/ml sheared and denatured herring sperm DNA, 0.02% ficoll, 0.02% polyvinylpyrrolidone, and 0.02% bovine serum albumin (Pentax Fraction V).

A preferred amplification buffer for Qβ replicase comprises the following: 40 mM Tris·HCl, pH 7.5, 10 mM $MgCl_2$, and 1 mM each of rATP, rGTP, UTP, and rCTP.

A hybridization/separation/amplification kit may also include buffers and other components (e.g., columns with gel) to carry out separation of hybridized from unhybridized probe.

EXAMPLE 2 (Kit 2)

Nuclease Protection/Amplification Kit

The Nuclease Protection/Amplification kit comprises at least three containers, packaged together, with the following components in separate containers:

(a) a hybridization buffer comprising an oligonucleotide probe with a complex amplifiable segment and the other properties described above for use in accordance with the nuclease protection/amplification method;

(b) an exonuclease buffer containing an exonuclease to catalyze degradation, in accordance with the nuclease protection/amplification method, of any probe that does not hybridize with target in an assay; and (c) an amplification buffer as in Kit 1.

A preferred hybridization buffer and amplification buffer are described above in the description of Kit 1.

A suitable exonuclease buffer comprises the following: 40 mM Tris·HCl, pH 7.5, 10 mM $MgSO_4$, and 0.1 mM dithiothreitol.

EXAMPLE 3 (Kit 3)

Ligation/Amplification Kit

The Ligation/Amplification Kit comprises, packaged together, at least two containers containing, in separate containers, the following components:

(a) a hybridization solution with the oligonucleotide probes, at least one of which is DNA or chimeric, which ligated together would comprise a complex amplifiable segment, and which have the other properties described supra for probes employed in accordance with the ligation/amplification methods of the invention; and (b) a ligase/amplification buffer containing T4 DNA ligase or other ligase and Qβ replicase or other RNA replicase (capable of amplifying via DDRP activity the amplifiable segment(s) occurring in the probes of component (a) when hybridized adjacent one another), said buffer being suitable for ligation with the ligase of single-stranded breaks in one strand of a double-stranded DNA and for DDRP activity of the replicase.

A preferred hybridization solution is described above in the description of Kit 1.

A preferred ligase/amplification buffer comprises the following: all of the components of the amplification buffer of Kit 1, plus 1 mM ATP, and 0.05 mg/ml bovine serum albumin.

Note that the amplification buffer of Kit 1 could be employed in place of the ligation/amplification buffer if probes hybridized to target are not to be ligated.

EXAMPLE 4 (Kit 4)

Double Extension/Amplification Kit

The Double Extension/Amplification Kit comprises, packaged together, at least three containers, with each of the following components in separate containers:

(a) a hybridization solution with the oligonucleotide probes, with the properties described hereinabove for the extension/amplification method, to yield a complex nucleic acid amplifiable via the DDRP activity of an RNA replicase;

(b) an extension buffer containing a DNA polymerase or reverse transcriptase to provide DNA polymerase activity; and (c) an amplification buffer as in Kit 1.

A preferred hybridization solution is described above in the description of Kit 1. A preferred extension buffer comprises the following: 40 mM Tris·HCl, pH 7.5, 10 mM $MgSO_4$, 0.1 mM dithiothreitol, and 0.04 mM each of dATP, dCTP, dGTP and TTP.

EXAMPLE 5 (Kit 5)

cDNA Synthesis/Amplification Kit

The cDNA Synthesis/Amplification Kit comprises, packaged together, at least four containers with each of the following components in separate containers:

(a) a hybridization solution with an RNA- or chimeric-amplifiable-segment containing oligonucleotide probe, as described hereinabove for the cDNA synthesis/ amplification method of the invention (see procedure 5, above) and the other probes that may be employed in embodiments of the method (see procedure 6 above);

(b) a reverse transcriptase buffer containing AMV reverse transcriptase, MMLV reverse transcriptase, or other reverse transcriptase, said buffer being suitable for catalysis of reverse transcription by the enzyme;

(c) a solution to degrade RNA or chimeric probe after reverse transcription primed by target on the probe; and (d) an amplification buffer as in Kit 1 with a replicase (e.g., Qβ replicase) capable of amplifying the amplifiable segment of the RNA or chimeric probe in component (a).

A preferred hybridization solution and amplification buffer are described above in the description of Kit 1. A preferred reverse transcriptase buffer comprises the following: 34 mM Tris·HCL, pH 8.3, 50 mM NaCl, 5 mM MgCl$_2$, 5 mM dithiothreitol, and 1 mM each of dATP, dGTP, TTP, and dCTP. A preferred RNA-degrading solution is 1 N NaOH.

EXAMPLE 6 (Kit 6)

Hybridization/Amplification Kit

The Hybridization/Amplification Kit is the same as the Hybridization/Separation/Amplification Kit (Kit 1) described above but includes no components for separation of hybridized from unhybridized probe.

Kits of the invention may also include reagents for detection, or other uses, of RNA produced in amplification in accordance with the invention.

As the skilled understand, diagnostic assays and other tests such as those contemplated in connection with the present invention are generally carried out on test sample(s) in parallel with suitable positive or negative "control" samples to insure that the reagents employed in the assays or tests are functioning properly to generate a signal indicative of the presence of an analyte, if analyte is present in a test sample, and to provide a level of "background" signal (typically signal from a control sample known to have none of the analyte), which signal obtained from a test sample must exceed before it can be concluded reliably that the test sample included analyte. Control samples can also be employed to provide a measure of signal as a function of the amount or concentration of analyte and, thereby, allow quantitation of the amount or concentration of analyte in test samples. Further, "control" analytes known to be present in test samples, in some cases at known concentrations (e.g., two beta-hemoglobin genes per normal red blood cell), or deliberately added to test samples, also possibly at known concentrations, can be employed to provide suitable controls or standards for quantitation in testing for analytes being tested for in test samples. The kits according to the invention, especially the test kits for analytes, may also include probes and other reagents to provide suitable controls for the use of the kits in determining the presence of or quantifying the amount of analytes in test samples.

The following examples are offered by way of illustration and are not intended to limit the invention in any manner.

EXAMPLES

Example 1

This is an example of amplification of a DNA employing the DDRP activity of an RNA replicase, Qβ replicase. The amplified DNA is a nanovariant DNA with the sequence specified in SEQ ID NO: 1, namely 5'-GGGGAAATCC TGTTACCAGG ATAACGGGGT TTTCTCACCT CTCTACTCGA AAGTTAGAGA GGACACACCC GGATCTAGCC GGGTCAACCC-3'. The nanovariant DNA with this sequence is referred to in the present specification as "nv(+)DNA". The nanovariant DNA with the sequence complementary to that of nv(+)DNA is referred to in the present specification as "nv(−)DNA". The 90-base pair double-stranded DNA, one strand of which is nv(+)DNA and the other strand of which is nv(−)DNA, is referred to in the present specification as "nvDNA". A 50 attomole sample of nv(+)DNA was amplified with the following steps: The 50 attomoles of nv(+)DNA was taken up in 10 μl final volume of a mixture containing the following:

10 M Tris·HCl, pH 7.5;
15 mM MgCl$_2$
1 mM each of the ribonucleoside triphosphates ATP, GTP, UTP, CTP; and
100 μg/ml Qβ replicase.

The mixture was incubated at 30° C. for 60 minutes, and transferred to a microtiter well containing 10 μl of a 2×concentrate of reaction stop solution (2×reaction stop solution: 100 mM EDTA, 0.2% NaPP$_i$ (i.e., sodium pyrophosphate), 1 μg/ml ethidium bromide). The reaction mixture was irradiated with medium wavelength (302 nm) ultraviolet light and the amplified product was visualized by means of the associated fluorescence. The fluorescence from the reaction mixture which contained the nv(+)DNA was compared with that from a control reaction mixture, which was prepared in the same way as the nv(+)DNA reaction mixture from a control sample, that was the same as the sample with the nv(+)DNA except that it lacked the nv(+) DNA.

The results indicated at least 100-fold more fluorescent material in the reaction mixture prepared with the nv(+) DNA-containing sample. This quanitative difference was determined by comparison of the fluorescence from the reaction mixtures with fluorescent standards consisting of diluted samples of herring sperm DNA analyzed under identical conditions.

Example 2

The product of the amplification reaction described in Example 1 was also analyzed by electrophoresis on an 8% polyacrylamide, 7M urea denaturing gel according to the following procedure. A 30 ml gel (0.4 mm thick) was prepared by mixing 76 g/l acrylamide, 8 g/l bis-acrylamide, 440 g/l urea, 500 μl/l TEMED in 1×TBE (1×TBE: 89 mM Tris base, 89 mM boric acid, 2 mM EDTA). To 30 ml of this solution was added 500 μl of a fresh solution of 10% ammonium persulfate. After gel polymerization, 5 μl samples of the nv(+)DNA amplification reaction mixture (which included 25 attomoles of nv(+) DNA) were treated, prior to loading on the gel, by being heated to 95° C. for 2 minutes in 20 μl blue juice (blue juice: 600 mg/ml urea, 1 mM EDTA, 5% glycerol, 0.05% bromophenol blue, 0.05% xylene cyanol). The gel was prerun for 30 minutes at 300 volts and, after loading of samples, was run at 400 volts for 1 hour. The gel was then stained for 20 minutes in a solution of 0.5 μg/ml ethidium bromide and nucleic acids were visualized by fluorescence, caused by exposure of the gel to ultraviolet light at 302 nm.

The results indicated that the product of the amplification reaction migrated as a single band at a position consistent with the amplification of a 90-base RNA. Because the product fluoresced in the presence of ethidium bromide and was synthesized using ribonucleoside triphosphates, it must have been RNA. The original DNA material prior to amplification (which would have been present at less than 1 pg in the solution as loaded on the gel) would not have been visible by this process.

The procedure for determining that the amplified material included both strands of RNA was as follows. Two stained gels were prepared as described above. Each was soaked for 20 minutes in 0.1 ×TBE containing 0.5 µg/ml ethidium bromide and the nucleic acid electrophoretically transferred to a Hybond membrane filter (Amersham, Cat. No. RPN. 203N, Arlington Heights, Ill., USA) for 10 minutes at 50 volts in 0.1×TBE. The filter was washed for 30 minutes at 65° C. in 0.1×SSC (1×SSC: 150 mM sodium chloride, 15 mM sodium citrate), 0.5% SDS. The filter was then prehybridized for 3 hours at 65° C. in 5×SSC, 40 mM NaPO$_4$, 5×Denhardt's Solution (1×Denhardt's Solution: 200 µg/ml each of ficoll, polyvinylpyrrolidone, and bovine serum albumin (BSA)), 0.1 mg/ml sheared and denatured herring sperm DNA, and 10% dextran sulfate. $^{32}$PO$_4$-kinased oligonucleotide PM618 (a 66-base DNA probe with the sequence of SEQ ID NO: 17, which is the same as that of the 66 bases at the 5'-end of nv(+)DNA) and $^{32}$PO$_4$-kiased oligonucleotide PM624 (a 66-base DNA probe with the sequence of SEQ ID NO: 18, which is complementary to the sequence of the 66 bases at the 3'-end of nv(+)DNA), respectively, were heated to 95° C. for 5 minutes and added for hybridization to the separate filters that had been prepared, washed and prehybridized as described, supra, (except that the filter used with PM618 had been previously used with another probe buT this probe had been stripped by exposure of the filter to three sequential 1 minute treatments at 100° C. with 0.1× SSC, 0.1% SDS). The mixtures were hybridized overnight at 65° C. Then, the filters were rinsed briefly with 2×SSC, 0.1% SDS, again with the same solution at room temperature for 15 minutes and again for 30 minutes. The filters were rinsed two more times for 30 minutes each at 65° C. in 0.1×SSC, 0.1% SDS and were exposed to Kodak XAR-5 film at −80° C. using two DuPont Cronex Hi Plus intensifier screens.

The results indicated strong hybridization of both the PM618 and PM624 to the products of the amplification reaction seen by ethidium stain described above. This indicates that both strands of nvRNA are made, fulfilling the final requirement of autocatalytic replication.

Additional support for the fact that DNA is amplified in the sample is derived from the following procedure, which eliminated RNA from the sample prior to amplification. One picomole each of nv(+)DNA and nv(+)RNA (the nanovariant RNA with the same sequence as nv(+)DNA) were incubated for various time periods, in parallel but separately, in 1 ml of 1 N NaOH at 80° C. The treatments with alkali were followed by neutralization with an equal volume of 1 N HCl, buffering by addition of Tris·HCl, pH 7.5 to a final concentration of 460 mM, and dilution such that, if no template had been degraded in the alkali treatment, template would have been present at one attomole per 10 µl. Then, amplification and detection procedures were carried out as described above. After 15 minutes of alkali treatment, nv(+) RNA was no longer amplifiable, as indicated by the lack of fluorescent material found after the amplification procedure was carried out. However, nv(+)DNA was amplifiable, after 15 or 60 minutes of alkali treatment, as indicated by at least a 100-times greater fluorescence intensity from the reaction mixture after the amplification procedure in comparison with such intensity from control samples lacking any template and the samples which contained only nv(+) RNA as template. After 180 minutes of the alkali treatment, the ability of nv(+)DNA to function as a template for amplification was also destroyed. Milder treatment of 15 minutes at 0.2 N NaOH at 37° C. can also be used to discriminate amplification of nv(+)RNA (or nv(−)RNA) template from that of nv(+)DNA (or nv(−)DNA) template.

An alternative treatment to destroy RNA present in samples, and therefore diminish autocatalytically replicatable RNA as template for amplification by an RNA replicase, without degrading DNA, including such DNA that might serve as a template for DDRP activity of such a replicase, is to treat with the nuclease RNAse A (10 µg/ml) for 20 minutes at 37° C. This is followed by addition of 200 units of RNasin® RNase inhibitor (Promega Corporation, Madison, Wis., USA) to neutralize the nuclease. For example, nv(+)DNA or nv(−)DNA samples treated in this manner retain their ability to be amplified via the DDRP activity of Qβ replicase.

Example 3

This example is directed to illustrating additional oligonucleotide single-stranded and double-stranded templates for amplification by Qβ replicase via its DNA-dependent RNA polymerase activity.

The amplification procedures of Example 1 are followed, except that the templates described in Table 1 are used in the quantities described in Table 1, and are amplified under the time and temperature conditions described in Table 1. Except for herring sperm and stool DNAs; quantities are in attomoles. The templates listed, other than those which are part of a plasmid, are single-stranded oligonucleotides. The nucleotide sequences of the individual templates, other than the plasmids and the herring sperm and stool DNAs, are described in the Sequence Listing. The "nv plasmid" is plasmid pNV-1-3-4 (see FIG. 8 and Example 6); in the linearized form, the plasmid was cut with a restriction endonuclease outside the segment of nanovariant DNA. The "description" is with reference to one strand, as indicated (or both strands, in the case of the nv plasmid) of nvDNA (see Example 1). The amplified material is placed in a microtiter dish and is visualized as described in Example 1. Amplification is indicated by a "+" sign, while lack of amplification is indicated by a "−" sign.

TABLE 1

| Template Sequence ID NO | Length bases | Strand | Description | Template Quantity attomoles | Assay Time min. | Conditions Temperature ° C. | Amplification Results |
|---|---|---|---|---|---|---|---|
| 1 | 90 | + | Full length | 50 | 60 | 30 | + |
| 2 | 88 | + | 3'-deietion | 50 | 30 | 37 | + |
| 3 | 78 | + | Internal deletion | 50 | 30 | 37 | + |

TABLE 1-continued

| Template Sequence ID NO | Length bases | Strand | Description | Template Quantity attomoles | Assay Time min. | Conditions Temperature °C. | Amplification Results |
|---|---|---|---|---|---|---|---|
| 4 | 67 | + | 3'-deletion | 50 | 60 | 30 | + |
| 5 | 87 | + | 5'-deletion | 50 | 60 | 37 | + |
| 6 | 90 | − | Full length | 50 | 60 | 30 | + |
| 7 | 129 | − | 3'-extension | 50 | 60 | 30 | + |
| 8 | 70 | − | 3'-deletion | 50 | 60 | 30 | + |
| 9 | 119 | + | Insertion | 50 | 60 | 30 | + |
| 10 | 138 | + | Insertion | 50 | 60 | 30 | + |
| nv plasmid supercoil | | Both | Extensions | 1 | 30 | 30 | + |
| nv plasmid linear | | Both | Extensions | 1 | 30 | 30 | + |
| herring sperm DNA | | None | No nv present | 1 ng | 30 | 30 | − |
| purified stool DNA | | None | No nv present | 0.01 ng | 60 | 60 | − |

Example 4

This example illustrates a ligation/amplification procedure. One μl of 200 mM NaCl containing 100 femtomoles of oligonucleotide PM754, 100 femtomoles of target nucleic acid PM2123, and 50 femtomoles of oligonucleotide PM2004 (see Sequence Listing for SEQ ID NOs 11, 21, 20 for the sequences of PM754, PM2123, and PM2004, respectively) was mixed with 2μl 10×ligase buffer (10× ligase buffer: 400 mM Tris·HCl, 100 mM $MgCl_2$, 10 mM DTT, 500 μg/ml acetylated BSA). The mixture was set at 70° C. and slow-cooled for 40 minutes to allow hybridization of the oligonucleotides to occur. 11 μl water, 2 μof a mix of 10 mM of each rNTP, and 1 μl T4 DNA ligase (2 units) were added and the entire mixture was set at 25° C. for 60 minutes. Two microliters of Qβ replicase (1.2 mg/ml) was added and amplification proceeded for 30 minutes at 30° C. The reaction was terminated by transfer of the entire sample into 20μl of 2×stop solution (see Example 1). The products of the reaction were visualized as described in Example 1. The products appeared as bright fluorescing material in microtiter wells. If the target molecule, PM2123, was left out of the reaction, fluorescence was very weak and similar to that observed in wells containing buffers but neither Qβ replicase nor probes.

The reaction products were analyzed following electrophoresis through an 8% polyacrylamide 7M urea denaturing gel according to the following procedure. A 40 ml gel (1.5 mm thick) was prepared by mixing 76 g/l acrylamide, 4 g/l bis-acrylamide, 500 g/l urea in 1×TBE. To 50 ml of this solution were added 25 μl of TEMED and 250 μl of a fresh solution of 10% ammonium persulfate. After gel polymerization, 5 μl samples of amplification reaction mixtures were prepared by heating to 95° C. for 1 minute in 25 μl blue juice (Example 2). The gel was prerun for 30 minutes at 30 mA and, after loading samples, was run at 30 mA for 1.5 hours. The gel was stained and visualized as described in Example 2. When the target, PM2123, was present in the reaction, two major bands, of approximately 118 and 110 bases in length, and at least 7 weaker bands, with lengths from about 80 to several hundred bases, were observed. These data indicate that the amplification of reporter molecules was dependent on the presence of target molecules in the sample.

Confirmation of target-specific amplification was demonstrated by hybridization of the electrophoretically separated material with probe PM407 according to the following procedure, For the sequence of PM407, see SEQ ID NO: 19 in the Sequence Listing. Nucleic acid from the stained gel was electrophoretically transferred to a Hybond membrane filter for 20 minutes at 45 volts in 0.1×TBE. The resulting filter was prehybridized for 1 hour at 65° C. as described in Example 2. $^{32}PO_4$-kinased oligonucleotide PM407 was added and the mixture was hybridized for 4 hours at 60° C. The filter was rinsed for one minute at room temperature in 2×SSC, 0.1% SDS and 5 times for 15 minutes each at 60° C. in 2×SSC, 0.1% SDS. The resulting filter was exposed to Kodak XAR-5 film at −80° C. using two DuPont Cronex Hi-Plus YE intensifier screens. Hybridization was observed only with the 118-base band.

In different experiments with target nucleic acid present, products of different lengths, from several tens to several hundred bases, and different distributions of amplification products among the various lengths, have been observed. It has been found that, in a given experiment, some of the products include a segment with the sequence complementary to that of target segment, as judged by hybridization with PM407, and some do not. However, in every experiment when target, PM2123, was present, at least some of the product included a segment with the sequence complementary to that of target segment. Further, in experiments in which PM2123 was not present, no reaction product that hybridized with PM407 was found.

Example 5

This example illustrates a target-dependent amplification process mediated by the DDRP activity of Qβ replicase following hybridization, but no ligation, of two probes which hybridize to adjacent segments of target nucleic acid and which both comprise a part of a segment of DNA which has the sequence of an RNA that is autocatalytically replicatable by the replicase. One microliter of 200 mM NaCl containing 100 femtomoles PM754, 100 femtomoles PM2123, and 50 femtomoles PM2004 was mixed with 2 μl 10×ligase buffer. The mixture was set at 70° C. and slow-cooled for 40 minutes to allow hybridization of the oligonucleotides to occur. Twelve microliters water, and 2 μl of a mix of 10 mM of each rNTP were added and the entire mixture was set at 25° C. for 60 minutes. Two microliters of Qβ replicase (1.2 mg/ml) was added and amplification proceeded for 30 minutes at 30° C. The reaction was terminated by transfer of the entire sample into 20 μl of 2×stop solution (see Example 1). The products of the reaction were visualized as described in Example 1.

The products appeared as bright fluorescing material in microtiter wells. If the target molecule, PM2123, was left out of the reaction, fluorescence was very weak and similar to that observed in wells containing buffers but neither the replicase nor probes. These data indicate that the amplification of reporter molecules was dependent on the presence of target molecules in the sample but did not require ligation of the probes hybridized adjacent one another on the target. The reaction products were analyzed following electrophoresis through a polyacrylamide-urea denaturing gel as described in Example 4. When PM2123 was present in the reaction, a single major band of approximately 90 bases in length was observed. Confirmation of target-specific amplification was demonstrated by hybridization of the electrophoretically separated material with probe PM407 as described in Example 4. Hybridization was observed only in the case of the 90-base reaction product generated in the presence of PM2123.

Example 6

This example illustrates the hybridization/separation/amplification procedure.

The target was a 107 nucleotide sequence of the E. coli lacZ gene which codes for a region at the amino terminus of the beta-galactosidase protein. The target region of the lacZ gene is contained in M13mp19 phage DNA (Yanisch-Perron, C., et al. (1985), Gene 33:103–119). DNA from the related phage, φX174, was used as a negative control. Phage φX174 DNA does not contain the lacZ gene.

Figure 8:
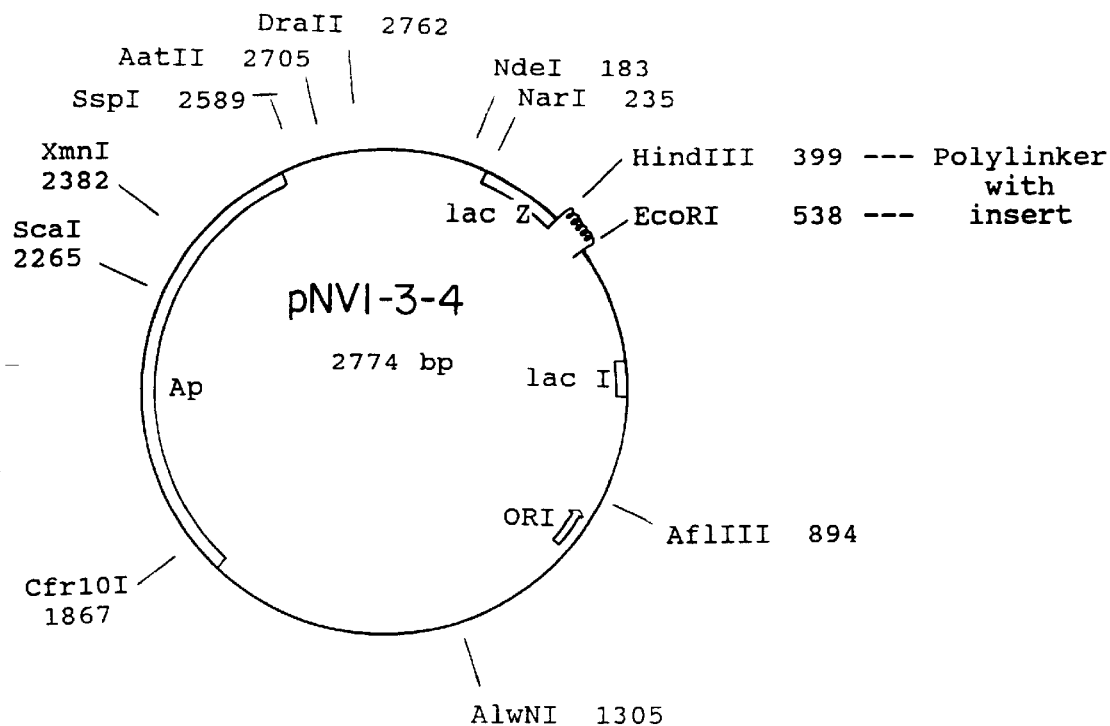
FIG. 8 illustrates a partial restriction site and functional map of the plasmid pNV1-3-4 and the sequence of a fragment from the plasmid which comprises a probe used in a method according to the invention, as described in Example 6.

The probe used in this example is isolated from the plasmid pNV1-3-4, which is illustrated in FIG. 8. pNV1-3-4 is a derivative of plasmid pUC18 (Yanisch-Perron, C., et al. (1985), Gene 33:103–119) and was constructed using standard techniques by replacing the small PstI-KpnI fragment of the polylinker of pUC18 with a segment providing the T7 RNA polymerase promoter and an nvDNA (double-stranded). The sequence of this promoter/nvDNA-containing segment is shown in FIG. 8. The nvDNA segment is indicated in the Figure as "nanovariant (+) strand," because the sequence of the nv(+)DNA is shown. Plasmid pNV1-3-4 carries, within a PvuII/SmaI restriction fragment, both a segment with the sequence complementary to the 107 base target site, described above, and the nvDNA segment.

The probe was prepared by sequential digestion of plasmid pNV1-3-4DNA with restriction endonucleases PvuII and SmaI, respectively. Approximately 56 micrograms of plasmid DNA was digested with 140 units of PvuII (Promega, Madison, Wis., USA) at 37° C. in SmaI digestion buffer (Promega) for 75 minutes in a final volume of 1 ml. The reaction was cooled to 25° C., 200 units of SmaI was added, and the digestion was allowed to continue for 5 hours at 25° C.

Approximately 13 µg (7 picomoles) of the digested DNA was dephosphorylated and labeled at the 5' terminus with $^{32}$P-ATP (3,000 Ci/mmole) using the reagents and conditions from the DNA 5' End Labeling Kit (Cat. No. 702757) from Boehringer Mannheim (Indianapolis, Ind., USA). The three labeled fragments (2.37 kb, 214 bp, and 194 bp) were separated on a 10% polyacrylamide/7M urea gel (see Example 2). The 214 bp fragment which contains the Qβ nvDNA segment, a T7 RNA polymerase promoter segment, and the 107 bp complementary to the target in the lacZ gene, was excised from the gel. The DNA was recovered from the gel by a modified "crush/elusion" method in which the gel fragment was placed in a LID/X test tube (LID/X Filter Syringe AQOR25, Genex, Gaithersburg, Md., USA) containing 0.4 ml of 100 mM NaCl, 0.1% SDS, 10 mM Tris·HCl, 1 mM EDTA, pH 8. The tube was sealed with the filter-plunger and mixed overnight at 37° C. The filtrate was recovered and 0.4 ml of fresh buffer was added to the filter syringe, mixed for 2 hours at room temperature and filtered again. The filtrates were combined and the probe concentration was determined by scintillation counting.

Approximately 2 picomols (0.3 ml) of the probe was mixed with 1 picomol (1 µl) of the target (or φX174, the negative control) and the mixture was ethanol precipitated. The resulting DNA pellet was dissolved in 0.1 ml of 2×SSC, 0.1% SDS. The probe and target (or negative control) were subjected to hybridization conditions by heating to 100° C. for five minutes, followed by slow cooling to 50° C., and maintaining the temperature at 50° C. for 90 minutes.

Following hybridization, the unhybridized probe was separated from phage DNA and hybrid molecules (i.e., probe-target hybrids) by gel filtration on a Bio-Gel A-5 (BioRad, Richmond, Calif., USA) column (1 cm×28 cm) in 100 mM NaCl, 10 mM Tris·HCl, 1 mM EDTA, pH 8.0. Eighty fractions (five drops each) were collected. The elution position of the phage DNA and the unhybridized probe were determined by separate chromatographic runs. The elution position of the phage DNA was determined by a fluorometric DNA assay using Hoechst 33258 (bis-benzimide) dye (Boehringer-Mannhein, Indianapolis, Ind.) (0.15 µg/ml dye in 150 mM NaCl, 10 mM Hepes, pH 7.5; excitation at 354 nm; emission at 454 nm; with a Perkin-Elmer LS-3 Fluorescence Spectrophotometer) from 40 µl aliquots of the column fractions. The elution position of the unhybridized DNA probe was determined by detection of either the $^{32}$P-label on the probe or the Qβ replication products amplified from the nvDNA segment within the probe.

Figure 9:
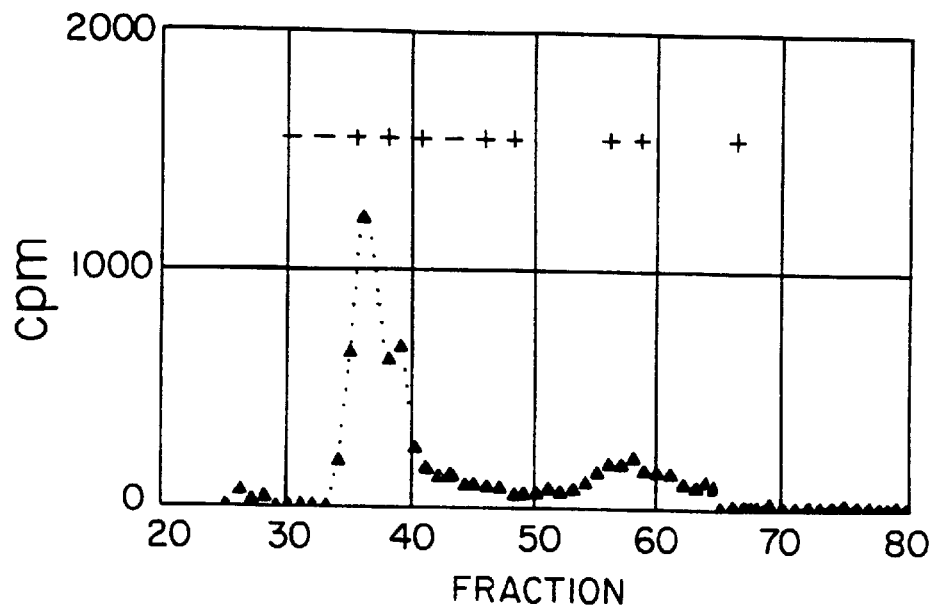
FIG. 9(a) and FIG. 9(b) are graphs representing the results of an amplification and detection procedure according to the invention with a nucleic acid (phage M13mp19 DNA), which comprises target segment for probe, and a nucleic acid (phage φX174 DNA) which lacks target segment for probe.
Figure 9:
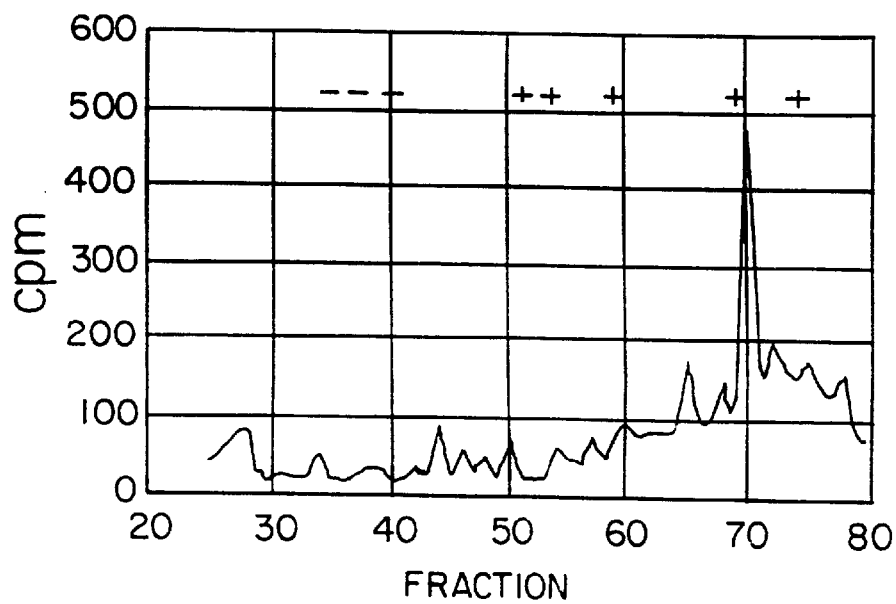

Referring now to FIGS. 9(a) and 9(b), the X-axes indicate fraction numbers from the columns and the Y-axes indicate the amount of radioactivity (cpm) present in each fraction. Particular fractions which were shown to amplify material in the presence of Qβ replicase are indicated by a plus (+) while those which were shown not to amplify material in the presence of Qβ replicase are indicated by a minus (−). FIG. 9a illustrates the results of hybridization with the fragment containing the target, and FIG. 9b shows the result of hybridization with the fragment which does not contain target.

Hybridization of probe to the lacZ gene in M13mp19 was indicated by the presence of the probe in the M13mp19 DNA peak and was determined by detection of the radioactive label and by the presence of DNA amplifiable by Qβ replicase as described in the next following paragraph.

Following separation of unhybridized probe from phage DNA and hybrid molecules, respectively, samples with φX174 DNA and with M13mp19 DNA (including hybrid molecules) were combined with ribonucleoside triphosphates and Qβ replicase for amplification in accordance with the procedure described in Example 1, except that products from amplification were measured with with a Perkin-Elmer fluorescence spectrophotometer measuring ethidium bromide fluorescence (0.5 µg/ml dye in water; excitation at 530 nm; emission at 600 nm).

Referring now to Table 2 below it will be seen that after hybridization with M13mp19 phage DNA, the hybrid DNA peak fraction contained 1230 cpm and produced 1485 fluorescence units of RNA after Qβ amplification. The specificity of the hybridization and detection steps were confirmed by the use of a nonhomologous mock target DNA (φX174 phage DNA). The peak that would have contained hybrid that was eluted from the Bio Gel A-5 column after hybridization with φX174 DNA contained only a background level of radioactively-labeled probe and no detectable RNA was produced by Qβ amplification.

TABLE 2

| Elution Position | CPM from $^{32}$P-Probe | Fluorescence of Qβ replicase products |
|---|---|---|
| Controls | | |
| M13mp19 Phage Peak | 23 | −1.5 |
| Probe Peak | 480 | 993.5 |
| Assay Background | 20 | −1.0 |
| After Hybridization with M13mp19 phage DNA | | |
| Phage Peak | 1230 | 1485 |
| Probe Peak | 1033 | 1033 |
| After Hybridization with φX174 phage DNA | | |
| Phage Peak | 27 | 0.4 |
| Probe Peak | 476 | 1369 |

Example 7

This example illustrates the cDNA synthesis/amplification procedure. In this example, the probe is (+) strand nvRNA while the target is a 21-base (−) strand DNA sequence which is complementary to the 3'-terminal 21 bases of the (+) strand nvRNA. Seventy-five picomoles of probe was mixed with either 750 picomoles, 75 picomoles, 800 femtomoles, 8 femtomoles, 80 attomoles, 800 tipomoles, 8 tipomoles, or 0 moles, respectively, of target in 5 μl of 1×SSC (150 mM NaCl, 15 mM sodium citrate) at 70° C. for 5 minutes to stimulate hybridization between the target and probe sequences. One microliter of this hybridization was diluted into a 20μl reaction mixture with final concentrations of 50 mM Tris·HCl, pH 8.3, 7.5 mM NaCl, 0.75 mM sodium citrate, 19 mM KCl, 10 mM MgCl$_2$, 10 mM DTT, 1 mM each dNTP and 2.2 units AMV reverse transcriptase/μl and incubated for 1 hour at 42° C. to synthesize a cDNA copy of the original RNA probe. The original RNA probe was destroyed by combining 9 μl of this mixture with 100 μl of 1 N NaOH at 90° C. for 15 minutes and then chilling the mixture on ice. The pH of the solution was neutralized by addition of 100 μl of 1 N HCl. Four microliters of this RNA-free cDNA solution were transferred to an amplification mix containing 100 mM Tris·HCl, pH 7.5, 100 mM NaCl, 15 mM MgCl$_2$,1 mM each of the four ribonucleoside triphosphates (i.e., rNTPs) ATP, GTP, UTP, and CTP, and 100 μg/ml Qβ replicase. The mixture was incubated at 30° C. for 60 minutes. The reaction products were visualized after denaturing polyacrylamide gel electrophoresis as described in Example 2.

Samples containing greater than or equal to 20 attomoles of target in the Qβ replicase reaction (which represents 8 femtomoles of target in the hybridization step) were detected by this method. Hybridization containing RNA probe with no target DNA produced no detectable product signal using this method.

Example 8

This example illustrates a ligationlamplification 30 procedure using purified Salmonella genomic DNA as target. The oligonucleotides PM1059 (with the sequence of SEQ ID NO: 24; compare with SEQ ID NO: 11 for the decanucleotide added at the 5'-end of PM754 to make PM1059) and PM764 (with sequence of SEQ ID NO: 12) were brought together by hybridization to adjacent sequences of Salmonella DNA and were ligated in a target-specific manner.

Oligonucleotide PM1059 was covalently attached at its 5' terminus to paramagnetic particles (Advanced Magnetics, Cat. No. 4100B, Cambridge, Mass., USA). Thirty microliters (30 μg) of PM1059 particles were concentrated for one minute using a magnetic concentrator (DYNAL, Catalog No. MPCE, Oslo, Norway) and were resuspended in 48 μl of hybridization solution (5×SSC, 1% BSA, 2% dextran sulfate, 0.1% Triton X-100) and prehybridized at 55° C. for 15 minutes. After 15 minutes, 1 μl (containing 1 femtomole) of PM764 and 2 μl (containing 330 ng or 100 am) of purified, denatured (by boiling for 5 minute) DNA from Salmonella typhimurium (ATCC No. 14028) was added to the hybridization solution. The hybridization proceeded for 1 hour at 55° C. After hybridization, the particles were magnetically concentrated for one minute and were washed twice with 2×SSC, 0.1% Triton X-100. Each wash involved adding 200 μl of wash solution, vortexing briefly to resuspend the particles, magnetically concentrating the PM1059 particles for one minute, and removing the wash solution. After removal of the second wash solution, the particles were resuspended in 50 μl of ligation/amplification buffer (ligation/amplification buffer: 40 mM Tris·HCl pH 7.8, 10 mM MgCl$_2$, 10 mM dithiothreitol, 100 μl/ml bovine serum albumin, 500 nM ATP, and 1 mM of each of the four rNTPs) and 5 Weiss units of T4 DNA ligase and were incubated at 30° C. for 1 hour. The ligated material was then amplified by the addition of 5 μl of Qβ replicase (1 mg/ml) to the ligation reaction and incubated at 30° C. for 1 hour. The reaction was terminated by adding 55 μl of 2×stop solution to the amplification reaction mixture.

The products of the amplification were analyzed on an 8% denaturing polyacrylamide gel as described in Example 2. The separated products were electrophoretically transferred to a Hybond nylon filter (Amershain, Cat. No. RPN. 203N) for 20 minutes at 40 volts in 0.1×TBE. The filter was visualized under ultraviolet light at 302 nm to confirm transfer of the stained products. RNA products on the filter were cross-linked to the filter by exposing the filter to 1200 μJ of ultraviolet light at 254 nm using a Stratalinker 1800 (Stratagene, Cat. No. 400071, La Jolla, Calif., USA). The filter was then prehybridized for one hour at 65° C. in 20 ml of hybridization solution B (5×SSC, 10% dextran sulfate, 100 μg/ml denatured herring sperm DNA, 40 mM NaPO$_4$, and 5×Denhardt's Solution). The probe for this hybridization was PM407 (see Table 1), with the sequence of SEQ ID NO: 19. Oligonucleotide PM407 corresponds to the Salmonella sequence present in oligonucleotide PM1059. Hybridization with this probe indicates presence of amplified ligated products because PM1059, alone, is not amplifiable. Probe PM407 was kinase labelled with $^{32}$PO$_4$ for 1 hour at 37° C. in a 10 μl volume. After heat killing the kinase at 90° C. for three minutes, the entire labelling reaction mixture was added to the hybridization solution and filter. The hybridization proceeded for four hours at 60° C. The filter was rinsed briefly with wash solution (2×SSC, 0.1% SDS) at room temperature followed by 5 15-minute washes with wash solution at 60° C. The filter was then exposed to Kodak XAR-5 film at −80° C. for 16 hours using two DuPont Cronex Lightning Plus intensifier screens.

The results indicate that PM407 hybridized to an RNA product that was approximately 120 bp in size. In a parallel ligation/amplification reaction in which the Salmonella target nucleic acid was not included, hybridization of the amplified products with the probe was not observed. This indicates that target specific ligation/amplification had occurred.

Example 9

This is an example of midivariant DNA amplification. The template used in this example, pMDV XhoI, is a double-stranded plasmid, pSP64 (Melton, D., et al. (1984) Nucl. Acids Res. 12:7035–7056), containing a segment with the sequence of a recombinant midivariant RNA (Mills, D. R., et al. (1978) Proc. Natl. Acad. Sci. U.S., 75,5334–5338) (FIG. 10). The sequence of the 274 bp HindIII-PstI fragment of pMDV XhoI is given by SEQ ID NO: 22. This fragment includes the mvDNA segment ("midivariant" DNA), which is from and including base pair 35 to and including base pair 266 of the sequence in SEQ ID NO: 22 and which has the sequence of a midivariant RNA (capable of being autocatalytically replicated by Qβ replicase) modified by an insertion of ten base pairs, CCTCGAGGAG, which includes an XhoI site, which is present at positions 66–75 of the midivariant sequence and positions 100–109 in SEQ ID NO: 22. Restriction endonuclease digestion with Pst I or Sma I, respectively, cleaves plasmid pMDV XhoI at the sites indicated at FIG. 10 Substrates were preincubated at 80° C. in 1 N NaOH for 15 minutes and neutralized by addition of an equivalent amount of HCl prior to their inclusion in replicase reactions to remove the potential for contamination with RNA templates. As a control experiment, a sample of each base-treated DNA template was also subjected to DNase treatment by addition of 5 units of RQ1 RNase-free DNase (Promega Corporation) for 60 minutes at 37° C.

Midivariant DNA-containing DNA served as a template for DNA-dependent RNA polymerization by Qβ replicase by addition of 1 femtomole of template in a 25 µl reaction vessel containing the following:

100 mM Tris·HCl, pH 7.5;

15 mM $MgCl_2$;

1 mM each of the ribonucleoside triphosphates ATP, GTP, UTP, CTP;

20 µg/ml Qβ replicase (Promega Corporation)

After addition of 5 microcurie (6.25 picomoles) α-$^{32}$P-CTP (DuPont Company, NEN Research Products, Boston, Mass.), the mixture was incubated for 60 minutes at 37° C. Amplification was monitored by spotting a portion of the reaction on a GFF filter (Whatman, Maidstone, England) precipitating the synthesized RNA by immersion of the filter in ice code 10% trichloroacetic acid/1% sodium pyrophosphate. The filters were washed four times with ice cold 5% trichloroacetic acid and then counted by liquid scintillation.

The results (Table 3) indicate the dependence of amplification on the presence of midivariant DNA sequences. They also indicate that molecules which have the standard 3' terminus exposed (Sma I-digested material) or those with the standard 3' terminus embedded within other DNA sequences (Pst I-digested material) both serve as amplifiable templates. In addition, undigested plasmids which are predominantly supercoiled also make effective substrates.

TABLE 3

DNA-DEPENDENT AMPLIFICATION OF MIDIVARIANT SEQUENCES

| | Picomoles of α-$^{32}$P-CTP incorporated | |
|---|---|---|
| Template | Base-Treated | Base-Treated DNAse Treated |
| pMDV XhoI (SmaI-digested | 460 | 7 |
| pMDV XhoI (PstI-digested) | 420 | 1 |
| pMDV XhoI (undigested) | 720 | 14 |

Example 10

This example is directed to the use of chimeric DNA-RNA templates for amplification via the DDRP activity of Qβ replicase.

The amplification and detection procedures of Example 1 were followed, except that 10, 1 or 0.1 tipomoles of the chimeric template, PM1070 (SEQ ID NO: 25), which has the same sequence as the nanovariant positive strand DNA (SEQ ID NO: 1) except that the 3 bases at the 5'-terminus and the 6 bases at the 3'-terminus are ribonucleotides, were amplified for 60 minutes at 30° C. Amplification was observed reproducibly with 1 or more tipomoles of the template and in some experiments carried out with 0.1 tipomoles of the template. No amplification was observed in the absence of template.

A second chimeric template, PM1500 (SEQ ID NO: 26), which has the same sequence as the nanovariant positive strand DNA sequence, except that bases 38, 39, 68 and 69 are ribonucleotides and the DNA 5'-ATAAGCGCCATTGATGTTGTCGCC-3' is joined to the 3'-terminus of the nv(+)DNA was also amplified.

The amplification procedure of Example 1 was followed except that 10 tipomoles of template, PM1500, was amplified for 60 minutes at 30° C. in 40 mM Tris·HCl, 10 mM DTT, 13 mM $MgCl_2$, 1 mM each rNTP, and 100 µg/ml Qβ replicase. The amplified material was placed in a microtiter dish and visualized as described in Example 1. Ten tipomoles of PM1500 amplified while there was no visible amplification in the absence of template.

Example 11

This example illustrates the sensitivity of amplification of nvDNA and nv-chimeric templates. A "chimeric" template is one which has both ribonucleotides and 2'-deoxyribonucleotides in its sequence.

Varying amounts of nvDNA (PM444) and nv-chimera (PM1070) were amplified for either 30 minutes or 60 minutes at 30° C. in 70 mM Tris·HCl, pH 7.6, 10 mM $MgCl_2$, 5 mM DTT (dithiothreitol), 1 mM of each rNTP, and 100 µg/ml Qβ replicase in a 10 µgl volume. Reactions were stopped by the addition of an equal volume of 2×stop solution. The reaction medium was irradiated and visualized as described in Example 1. The least amount of each template amplified under each condition is shown in Table 4.

TABLE 4

| Template | Time | Sensitivity |
| --- | --- | --- |
| PM444 | 30 min | 300 tipomoles |
| PM444 | 60 min | 30 tipomoles |
| PM1070 | 30 min | ≦10 tipomoles |
| PM1070 | 60 min | 1 tipomole |

Example 12

This example illustrates the sensitivity of amplification of an mdvDNA template.

Varying amounts of mdvDNA (gel purified Pst I/Sma I fragment of pMDV XhoI, FIG. 10) were base-treated, amplified, and detected as described in Example 9, except that amplification was performed at 30° C. The results are shown in Table 5.

TABLE 5

| Tipomoles of Template | Picomoles of CTP Incorporated |
| --- | --- |
| 100,000 | 920 |
| 1000 | 710 |
| 10 | 165 |
| 0.1 | 44 |
| 0 | 11 |

Example 13

This example illustrates the sensitivity of amplification of DNA and chimeric templates in the presence of manganese chloride.

Varying amounts of nvDNA (PM444) and nv-chimera (PM1070) were amplified for either 30 minutes or 60 minutes at 30° C. in 70 mM Tris·HCl, pH 7.6, 10 mM $MgCl_2$, 1 mM $MnCl_2$, 5 mM DTT, 1mM each rNTP, and 100 µg/ml Qβ replicase in a 10 µl volume. Reactions were stopped and visualized as described in Example 11 The reaction products were analyzed following electrophoresis through a polyacrylamide-urea denaturing gel as described in Example 2. In the presence of $MnCl_2$, amplification in the absence of template occurs after 30 minute or 60 minute reactions. However, the reactions produce a mixture of nucleic acid products of various sizes, which we refer to as "de novo" synthesis. See Biebricher et al. (1986) Nature 321, 89–91. When bona fide template is present and amplified, a product which migrates as a 90-base product is visible above the background of de novo synthesis. Confirmation of template-specific amplification was demonstrated by hybridization of the electrophoretically separated material with probe PM624 as described in Example 2. Hybridization was observed only in the cases where template was present and amplified. Hybridization did not occur with products generated by de novo synthesis.

The least amount of each template consistently amplified under each condition is shown in Table 6.

TABLE 6

| Template | Time | Sensitivity |
| --- | --- | --- |
| PM444 | 30 min | 10 tipomoles |
| PM444 | 60 min | 10 tipomoles |

TABLE 6-continued

| Template | Time | Sensitivity |
| --- | --- | --- |
| PM1070 | 30 min | 1 tipomoles |
| PM1070 | 60 min | 1 tipomoles |

Similar results were obtained with 0.5 mM $MnCl_2$ in the reaction mixture. With 2 mM $MnCl_2$ in the reaction mixture, the minimum detectable amount of target that was consistently observable remained the same as, but the amount of 90-base, target-segment-containing product from the amplification (over the same length of time) was less than, that observed when 1 mM $MnCl_2$ was used. With 0.25 mM $MnCl_2$, little or no effect on sensitivity or rate of production of the 90-base, target-segment-containing amplification product was observed, in comparison with the sensitivity and rate of-production when no $MnCl_2$ was used.

Example 14

This example illustrates the sensitivity of amplification of nvDNA template in the presence of cobalt chloride.

Varying amounts of nvDNA (PM444) were amplified for 30 minutes at 30° C. in 70 mM Tris·HCl, pH 7.6, 10 mM $MgCl_2$, 1 mM $CoCl_2$, 1 mM of each rNTP, and 100 µg/ml Qβ replicase in a 10 µl volume. Reactions were stopped and visualized as described in Example 11. The reaction products were analyzed by electrophoresis through a polyacrylamide-urea denaturing gel as described in Example 2. In the presence of $CoCl_2$, amplification in the absence of template occurs within 30 minutes, giving rise to a mixture of nucleic acid products of various sizes due to de novo synthesis. When bona fide template is present and amplified, one or more prominent products which migrate at positions corresponding to about 90 bases are seen above the background of de novo synthesis. Confirmation of template-specific amplification was demonstrated by hybridization of the electrophoretically separated material with probe PM624 as described in Example 2. Hybridization was observed only in the cases where at least 1 tipomole of template was present. Hybridization did not occur with products generated by de novo synthesis.

While the invention is described in the present specification with considerable specificity, those of skill in the art will recognize many variations and modifications of what has been described that remain within the spirit of the invention. It is intended that such modifications and variations also be encompassed by the invention as described and claimed herein.

What is claimed is:

1. A nucleic acid molecule comprising the sequence set forth in the SEQ ID NO:, the SEQ ID NO: selected from the group consisting of SEQ ID NO: 11, SEQ ID NO: 20, SEQ ID NO: 24, SEQ ID NO: 12, SEQ ID NO: 7, SEQ ID NO: 9, SEQ ID NO: 10, and SEQ ID NO: 22.

2. A nucleic acid according to claim 1, wherein the molecule comprises the sequence set forth in SEQ ID NO: 11.

3. A nucleic acid according to claim 1, wherein the molecule comprises the sequence set forth in SEQ ID NO: 20.

4. A nucleic acid according to claim 1, wherein the molecule comprises the sequence set forth in SEQ ID NO: 24.

5. A nucleic acid according to claim 1, wherein the molecule comprises the sequence set forth in SEQ ID NO: 12.

6. A nucleic acid according to claim 1, wherein the molecule comprises the sequence set forth in SEQ ID NO: 7.

7. A nucleic acid according to claim 1, wherein the molecule comprises the sequence set forth in SEQ ID NO: 9.

8. A nucleic acid according to claim 1, wherein the molecule comprises the sequence set forth in SEQ ID NO: 10.

9. A nucleic acid according to claim 1, wherein the molecule comprises the sequence set forth in SEQ ID NO; 22.

10. A nucleic acid molecule consisting essentially of the sequence set forth in the SEQ ID NO:, the SEQ ID NO: selected from the group consisting of SEQ ID NO: 11, SEQ ID NO: 20, SEQ ID NO: 24, SEQ ID NO: 12, SEQ ID NO: 7, SEQ ID NO: 9, SEQ ID NO: 10, and SEQ ID NO: 22.

11. A nucleic acid molecule selected from the group of nucleic acid molecules consisting of SEQ ID NO: 11, SEQ ID NO: 20, SEQ ID NO: 24, SEQ ID NO: 12, SEQ ID NO: 7, SEQ ID NO: 9, SEQ ID NO: 10, and SEQ ID NO: 22.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 90 base pairs
      (B) TYPE: nucleic acid
      (C) STRANDEDNESS: single
      (D) TOPOLOGY: linear (xi) SEQUENCE DESCRIPTION: SEQ ID NO:1:

GGGGAAATCC TGTTACCAGG ATAACGGGGT TTTCTCACCT                              40

CTCTACTCGA AAGTTAGAGA GGACACACCC GGATCTAGCC                              80

GGGTCAACCC                                                              90

(2) INFORMATION FOR SEQ ID NO:2:

(i) SEQUENCE CHARACTERISTICS:
      (A) LENGTH: 88 base pairs
      (B) TYPE: nucleic acid
      (C) STRANDEDNESS: single
      (D) TOPOLOGY: linear (xi) SEQUENCE DESCRIPTION: SEQ ID NO:2:

GGGGAAATCC TGTTACCAGG ATAACGGGGT TTTCTCACCT                              40

CTCTACTCGA AAGTTAGAGA GGACACACCC GGATCTAGCC                              80

GGGTCAAC                                                                88

(2) INFORMATION FOR SEQ ID NO:3:

(i) SEQUENCE CHARACTERISTICS:
      (A) LENGTH: 78 base pairs
      (B) TYPE: nucleic acid
      (C) STRANDEDNESS: single
      (D) TOPOLOGY: linear (xi) SEQUENCE DESCRIPTION: SEQ ID NO:3:

GGGGAAATCC TGTTACCAGG ATAACGGGGT TTTCTCACCT                              40

CTCTACTCGA AAGTTAGAGA GGACACACCC GGATCTAG                                78

(2) INFORMATION FOR SEQ ID NO:4:

(i) SEQUENCE CHARACTERISTICS:
      (A) LENGTH: 67 base pairs
      (B) TYPE: nucleic acid
      (C) STRANDEDNESS: single
      (D) TOPOLOGY: linear (xi) SEQUENCE DESCRIPTION: SEQ ID NO:4:

GGGGAAATCC TGTTACCAGG ATAACGGGGT TTTCTCACCT                              40

CTCTACTCGA AAGTTAGAGA GGACACA                                           67

(2) INFORMATION FOR SEQ ID NO:5:

(i) SEQUENCE CHARACTERISTICS:
      (A) LENGTH: 87 base pairs
      (B) TYPE: nucleic acid
      (C) STRANDEDNESS: single
      (D) TOPOLOGY: linear (xi) SEQUENCE DESCRIPTION: SEQ ID NO:5:

GAAATCCTGT TACCAGGATA ACGGGGTTTT CTCACCTCTC                    40

TACTCGAAAG TTAGAGAGGA CACACCCGGA TCTAGCCGGG                    80

TCAACCC                                                        87

(2) INFORMATION FOR SEQ ID NO:6:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (xi) SEQUENCE DESCRIPTION: SEQ ID NO:6:

GGGTTGACCC GGCTAGATCC GGGTGTGTCC TCTCTAACTT                    40

TCGAGTAGAG AGGTGAGAAA ACCCCGTTAT CCTGGTAACA                    80

GGATTTCCCC                                                     90

(2) INFORMATION FOR SEQ ID NO:7:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (xi) SEQUENCE DESCRIPTION: SEQ ID NO:7:

GGGTTGACCC GGCTAGATCC GGGTGTGTCC TCTCTAACTT                    40

TCGAGTAGAG AGGTGAGAAA ACCCCGTTAT CCTGGTTACA                    80

GGATTTCCCC TATAGTGTCA CCTAAATTTC ACCTCTGCCT                   120

AATCATCTC                                                    129

(2) INFORMATION FOR SEQ ID NO:8:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:8:

GGGTTGACCC GGCTAGATCC GGGTGTGTCC TCTCTAACTT                    40

TCGAGTAGAG AGGTGAGAAA ACCCCGTTAT                               70

(2) INFORMATION FOR SEQ ID NO:9:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (xi) SEQUENCE DESCRIPTION: SEQ ID NO:9:

GGGGAAATCC TGTTAGGATC CAGGATAACG GGGTTTTCTC                    40

ACCTCTCTAT CTAGGGCGAC AACATCAATG GCGCTTATAA                    80

AGTTAGAGAG GACACACCCG GATCTAGCCG GGTCAACCC                    119

(2) INFORMATION FOR SEQ ID NO:10:

(i) SEQUENCE CHARACTERISTICS:
    (A) LENGTH: 138 base pairs
    (B) TYPE: nucleic acid
    (C) STRANDEDNESS: single
    (D) TOPOLOGY: linear (xi) SEQUENCE DESCRIPTION: SEQ ID NO:10:

```
GGGGAAATCC TGTAACCAGG ATAACGGGGT TTTCTCAATA              40
AGCGCCATTG ATGTTGTCGC CTTTGTACGG CATACGGCCT              80
AACCACCTCT CTACTCGAAA GTTAGAGAGG ACACACCCGG             120
ATCTAGCCGG GTCAACCC                                     138
```

(2) INFORMATION FOR SEQ ID NO:11:

(i) SEQUENCE CHARACTERISTICS:
       (A) LENGTH: 61 base pairs
       (B) TYPE: nucleic acid
       (C) STRANDEDNESS: single
       (D) TOPOLOGY: linear (xi) SEQUENCE DESCRIPTION: SEQ ID NO:11:

```
GGGGAAATCC TGTAACCAGG ATAACGGGGT TTTCTCAATA              40
AGCGCCATTG ATGTTGTCGC C                                  61
```

(2) INFORMATION FOR SEQ ID NO:12:

(i) SEQUENCE CHARACTERISTICS:
       (A) LENGTH: 77 base pairs
       (B) TYPE: nucleic acid
       (C) STRANDEDNESS: single
       (D) TOPOLOGY: linear (xi) SEQUENCE DESCRIPTION: SEQ ID NO:12:

```
TTTGTACGGC ATACGGCCTA ACCACCTCTC TACTCGAAAG              40
TTAGAGAGGA CACCCGGA TCTAGCCGGG TCAACCC                   77
```

(2) INFORMATION FOR SEQ ID NO:13:

(i) SEQUENCE CHARACTERISTICS:
       (A) LENGTH: 61 base pairs
       (B) TYPE: nucleic acid
       (C) STRANDEDNESS: single
       (D) TOPOLOGY: linear (xi) SEQUENCE DESCRIPTION: SEQ ID NO:13:

```
GGGGAAATCC TGTTACCAGG ATAACGGGGT TTTCTCAGGT              40
CAACTGAACG CCCTGAGCTT T                                  61
```

(2) INFORMATION FOR SEQ ID NO:14:

(i) SEQUENCE CHARACTERISTICS:
       (A) LENGTH: 57 base pairs
       (B) TYPE: nucleic acid
       (C) STRANDEDNESS: single
       (D) TOPOLOGY: linear (xi) SEQUENCE DESCRIPTION: SEQ ID NO:14:

```
ATAAGCGCCA TTGATGTTGT CGCCCCTCTC TACTCGAAAG              40
TTAGAGAGGA CACACCC                                       57
```

(2) INFORMATION FOR SEQ ID NO:15:

(i) SEQUENCE CHARACTERISTICS:
    (A) LENGTH: 48 base pairs
    (B) TYPE: nucleic acid
    (C) STRANDEDNESS: single
    (D) TOPOLOGY: linear (xi) SEQUENCE DESCRIPTION: SEQ ID NO:15:

```
TGGTTAGGCC GTATGCCGTA CAAAGGCGAC AACATCAATG                40

GCGCTTAT                                                   48
```

(2) INFORMATION FOR SEQ ID NO:16:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:16:

```
GGCGACAACA TCAATGGCGC TTATAAAGCT CAGGGCGTTC                40

AGTTGACC                                                   48
```

(2) INFORMATION FOR SEQ ID NO:17:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:17:

```
GGGGAAATCC TGTTACCAGG ATAACGGGGT TTTCTCACCT                40

CTCTACTCGA AAGTTAGAGA GGACAC                               66
```

(2) INFORMATION FOR SEQ ID NO:18:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:18:

```
GGGTTGACCC GGCTAGATCC GGGTGTGTCC TCTCTAACTT                40

TCGAGTAGAG AGGTGAGAAA ACCCCG                               66
```

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:19:

```
ATAAGCGCCA TTGATGTTGT CGCC                                 24
```

(2) INFORMATION FOR SEQ ID NO:20:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:20:

```
TTTGTACGGC ATACGGCCTA ACCACCTCTC TACTCGAAAG                            40

TTAGAGAGGA CACACCC                                                     57
```

(2) INFORMATION FOR SEQ ID NO:21:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:21:

```
TGGTTAGGCC GTATGCCGTA CAAAGGCGAC AACATCAATG                            40

GCGCTTAT                                                               48
```

(2) INFORMATION FOR SEQ ID NO:22:

(i) SEQUENCE CHARACTERISTICS:
        (A) LENGTH: 274 base pairs
        (B) TYPE: nucleic acid
        (C) STRANDEDNESS: double
        (D) TOPOLOGY: linear (ix) FEATURE:
        (D) OTHER INFORMATION: Sequence is that of HindIII-EcoRI
            fragment, thought to be 274 bp in length, of plasmid pMDV
            XhoI. Both strands of the segment between bases 35-266,
            inclusive, as indicated in the sequence, are $Q_-$replicase
            amplifiable. The "N's" at bases 7 and 51 are,
            independently, either G or no base.
            The "NN" at bases 260 and 261 are GG, C or no bases.
            It is not known whether the K at base 262 is a T or a G.

(xi) SEQUENCE DESCRIPTION: SEQ ID NO:22:

```
AAGCTTNGGC TGCAGTCTAA TACGACTCAC TATAGGGGAC                            40

CCCCCCGGAA NGGGGGGACG AGGTGCGGGC ACCTGCTACG                            80

GGAGTTCGAC CGTGACGAGC CTCGAGGAGT CACGGGCTAG                           120

CGCTTTCGCG CTCTCCCAGG TGACGCCTCG TGAAGAGGCG                           160

CGACCTTCGT GCGTTTCGGT GACGCACGAG AACCGCCACG                           200

CTGCTTCGCA GCGTGGCCCC TTCGCGCAGC CCGCTGCGCG                           240

AGGTGACCCC CCGAAGGGGN NKTCCCGGGA ATTC                                 274
```

(2) INFORMATION FOR SEQ ID NO:23:

(i) SEQUENCE CHARACTERISTICS:
        (A) LENGTH: 232 base pairs
        (B) TYPE: nucleic acid
        (C) STRANDEDNESS: double
        (D) TOPOLOGY: linear (ix) FEATURE:
        (D) OTHER INFORMATION: Sequence is that of a midivariant DNA,
            thought to be 232 bases in length (base pairs 35 - 266 of
            the DNA fragment described in SEQ ID NO: 1. The "N" at
            base 17 is either G or no base. The "NN" at bases 226
            and 227 are GG, C or no bases. It is not known whether
            the K at base 228 is a T or a G.

(xi) SEQUENCE DESCRIPTION: SEQ ID NO:23:

```
GGGGACCCCC CCGGAANGGG GGGACGAGGT GCGGGCACCT                            40

GCTACGGGAG TTCGACCGTG ACGAGCCTCG AGGAGTCACG                            80
```

-continued

```
GGCTAGCGCT TTCGCGCTCT CCCAGGTGAC GCCTCGTGAA                    120

GAGGCGCGAC CTTCGTGCGT TTCGGTGACG CACGAGAACC                    160

GCCACGCTGC TTCGCAGCGT GGCCCCTTCG CGCAGCCCGC                    200

TGCGCGAGGT GACCCCCCGA AGGGGNNKTC CC                            232

(2) INFORMATION FOR SEQ ID NO:24:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:24:

CCTAGTCCAA GGGGAAATCC TGTTACCAGG ATAACGGGGT                     40

TTTCTCAATA AGCGCCATTG ATGTTGTCGC C                              71

(2) INFORMATION FOR SEQ ID NO:25:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ix) FEATURE:
        (D) OTHER INFORMATION: The three nucleotides at the 5'-end
            and the six nucleotides at the 3'-end are
            ribonucleotides.

(xi) SEQUENCE DESCRIPTION: SEQ ID NO:25:

GGGGAAATCC TGTTACCAGG ATAACGGGGT TTTCTCACCT                     40

CTCTACTCGA AAGTTAGAGA GGACACACCC GGATCTAGCC                     80

GGGTCAACCC                                                      90

(2) INFORMATION FOR SEQ ID NO:26:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ix) FEATURE:
        (D) OTHER INFORMATION: The nucleotides at positions 38, 39,
            68 and 69 are ribonucleotides.

(xi) SEQUENCE DESCRIPTION: SEQ ID NO:26:

GGGGAAATCC TGTTACCAGG ATAACGGGGT TTTCTCACCT                     40

CTCTACTCGA AAGTTAGAGA GGACACACCC GGATCTAGCC                     80

GGGTCAACCC                                                      90
```